United States Patent [19]

Gange et al.

[11] Patent Number: 5,180,419

[45] Date of Patent: Jan. 19, 1993

[54] HERBICIDAL 2-(2-IMIDAZOLIN-2-YL)-BENZO-(5-MEMBERED)-HETEROCYCLES AND THE USE THEREOF

[75] Inventors: David M. Gange, Princeton; Michael A. Guaciaro, Hightstown; Robert F. Doehner, Jr., East Windsor, all of N.J.

[73] Assignee: American Cyanamid Company, Stamford, Conn.

[21] Appl. No.: 797,479

[22] Filed: Nov. 22, 1991

Related U.S. Application Data

[63] Continuation-in-part of Ser. No. 576,645, Aug. 31, 1990, abandoned.

[51] Int. Cl.[5] .................... A01N 43/90; A01N 43/76; A01N 43/50; C07D 233/70; C07D 235/00; C07D 263/56; C07D 263/58

[52] U.S. Cl. .................... 504/276; 548/300.7; 548/311.4; 548/311.7; 548/147; 548/149; 548/171; 548/178; 548/180; 548/207; 548/209; 548/216; 548/217; 548/218; 548/221; 548/241; 548/242; 548/301.1; 548/301.7; 504/277; 504/191; 504/266; 504/267; 504/269; 504/270; 504/271; 504/248; 504/225

[58] Field of Search ............... 548/302, 149, 218, 301, 548/217, 180; 71/90, 92

[56] References Cited

U.S. PATENT DOCUMENTS 4,297,128  10/1981  Los .
4,608,079  8/1986  Los .

Primary Examiner—Mary C. Lee
Assistant Examiner—Michael G. Ambrose
Attorney, Agent, or Firm—John W. Hogan, Jr.

[57] ABSTRACT

There are provided o-carboxy-(5-oxo-2-imidazolin-2-yl)benzo-(5-membered)-heterocyclic compounds and derivatives thereof and a method for the use therewith to control monocotyledenous and dicotyledenous plant species.

16 Claims, No Drawings

HERBICIDAL 2-(2-IMIDAZOLIN-2-YL)-BENZO-(5-MEMBERED)-HETEROCYCLES AND THE USE THEREOF

BACKGROUND OF THE INVENTION

The present application is a continuation-in-part of application Serial No. 07/576,645, filed on Aug. 31, 1990, now abandoned..

Certain imidazolinyl benzoic and naphthoic acids, esters and salts and their use as herbicidal agents are described in U.S. patents 4,188,487; 4,297,128 and 4,554,013 and in patent applications GB 2 172 866 A and EP 86200304.3 However, the imidazolinyl benzoheterocycles of the present invention are not described nor suggested in said patents and patent applications. Fused heteropyridine compounds and their herbicidal use are described in U.S. Pat. Nos. 4,650,514 and 4,752,323 and copending U.S. application Ser. No. 465,569 filed on Jan. 16, 1990. Although a variety of herbicidally active imidazolinyl compounds are known, still more effective imidazolinyl compounds would be useful to farmers, agriculturalists, industrialists and the like for the control of undesirable plant species.

It is an object of the present invention to provide effective herbicidal imidazolinyl o-carboxy-2-benzoheterocyclic compounds and indoloheterocyclic diones for controlling a variety of monocotyledenous and dicotyledenous plant species such as those species which are generally difficult to control in agronomic practice.

SUMMARY OF THE INVENTION

The present invention relates to 2-(2-imidazolin-2-yl) benzoheterocyclic compounds having the structure

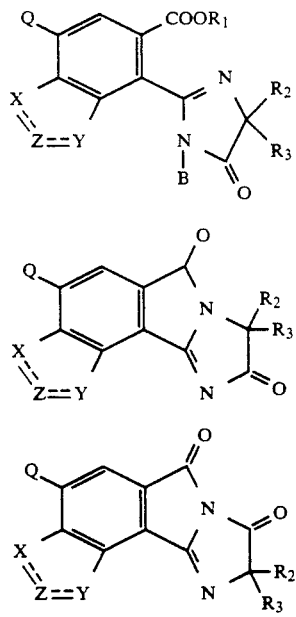

wherein $R_1$ is hydrogen, di($C_1$-$C_4$) alkylimino,
$C_1$-$C_{12}$ alkyl optionally substituted with one to three of the following: $C_1$-$C_4$ alkoxy, $C_1$-$C_4$ alkylthio, halogen, hydroxy, $C_3$-$C_6$ cycloalky, benzyloxy, furyl, phenyl, optionally substituted with one nitro, one to three halogens, $C_1$-$C_4$ alkyl groups or $C_1$-$C_4$ alkoxy groups, carboxy, $C_1$-$C_4$ alkoxycarbonyl, cyano or tri($C_1$-$C_4$) alkylammonium halide, $C_3$-$C_{12}$ alkenyl optionally substituted with one to three of the following: $C_1$-$C_4$ alkoxy, phenyl, halogen or $C_1$-$C_4$ alkoxycarbonyl, $C_3$-$C_6$ cycloalkyl optionally substituted with one to three $C_1$-$C_4$ alkyl groups, $C_3$-$C_{16}$ alkynyl optionally substituted with one to three halogens or a cation;

$R_2$ is $C_1$-$C_4$ alkyl;

$R_3$ is $C_1$-$C_4$ alkyl or $C_3$-$C_6$ cycloalkyl, and when $R_2$ and $R_3$ are taken together with the carbon to which they are attached they may represent $C_3$-$C_6$ cycloalky optionally substituted with methyl;

B is hydrogen, $COR_4$ or $SO_2R_5$ with the proviso that when B is $COR_4$ or $SO_2R_5$, $R_3$ is other than hydrogen or a cation;

$R_4$ is $C_1$-$C_{11}$ alkyl, chloromethyl or phenyl optionally substituted with halogen, nitro or $C_1$-$C_4$ alkyl;

$R_5$ is $C_1$-$C_4$ alkyl or phenyl optionally substituted with $C_1$-$C_4$ alkyl; X, Y and Z are each independently $CR_6$, $CR_7R_8$, $NR_9$, N, O or S with the proviso that at least one of X, Y, and Z must be O or S, at least one of X, Y, and Z must be $CR_6$ or $CR_7R_8$, when X or Y are O or S, then Z cannot be O or S and when X and Y are both O and Z is $CR_7R_8$, the structure must be a, c or e;

the ----- configuration represents either a signal bond or a double bond with the proviso that when any of X, Y, and Z is $CR_7R_8$, $NR_9$, O or S, then the ----- configuration attached thereto represents a single bond and with the further proviso that at least one of the ----- configurations represents a single bond;

$R_6R_7$, and $R_8$ are independently hydrogen, halogen, $C_1$-$C_4$ alkoxy or $C_1$-$C_4$ alkyl optionally substituted with one hydroxy or one to three halogens, $C_1$-$C_4$ alkoxy groups or $C_1$-$C_4$ alkylthio groups;

Q is hydrogen, halogen, $C_1$-$C_4$ alkoxy or $C_1$-$C_4$ alkyl optionally substituted with one to three of the following: halogen, $C_1$-$C_4$ alkoxy, $C_1$-$C_4$ alkylthio or $C_2$-$C_4$ alkenyl;

the optical isomers thereof when $R_2$ and $R_3$ are not the same or when $R_7$ and $R_8$ are not the same;

the tautomers and geometric isomers thereof and the acid addition salts thereof except when $R_1$ is salt forming cation.

The present invention further provides processes for the preparation of the above-said compounds and methods for controlling undesirable monocotyledenous and dicotyledenous plant species therewith.

Related benzoheterocyclic compounds and their herbicidal use are described in co-pending patent applications, Ser. No. 576,621 and 576,643, both filed on Aug. 31, 1990 and incorporated herein by reference thereto.

DESCRIPTION OF THE INVENTION

This invention relates to 2-(2-imidazolin-2-yl)benzoheterocyclic compounds having the structure

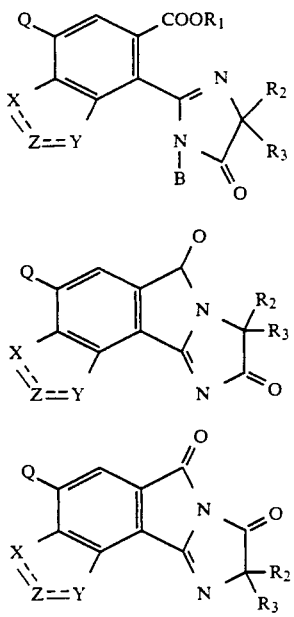

wherein
R₁ is hydrogen, di(C)alkylimino,
C₁-C₁₂ alkyl optionally substituted with one to three of the following: C₁-C₄ alkoxy, C₁-C₄ alkylthio, halogen, hydroxy, C₃-C₆ cycloalkyl, benzyloxy, furyl, phenyl, optionally substituted with one nitro, one to three halogens, C₁-C₄ alkyl groups or C₁-C₄ alkoxy groups, carboxy, C₁-C₄ alkoxycarbonyl, cyano or tri(C₁-C₄)alkylammonium halide,
C₃-C₁₂ alkenyl optionally substituted with one to three of the following: C₁-C₄ alkoxy, phenyl, halogen or C₁-C₄ alkoxycarbonyl,
C₃-C₆ cycloalkyl optionally substituted with one to three C₁-C₄ alkyl groups,
C₃-C₁₆ alkynyl optionally substituted with one to three halogens or a cation;
R₂ is C₁-C₄ alkyl;
R₃ is C₁-C₄ alkyl or C₃-C₆ cycloalkyl, and when R₂ and R₃ are taken together with the carbon to which they are attached they may represent C₃-C₆ cycloalkyl optionally substituted with methyl;
B is hydrogen, COR₄ or SO₂R₅ with the proviso that when B is COR₄ or SO₂R₅, R₃ is other than hydrogen or a cation;
R₄ is C₁-C₁₁ alkyl, chloromethyl or phenyl optionally substituted with halogen, nitro or C₁-C₄ alkyl;
R₅ is C₁-C₄ alkyl or phenyl optionally substituted with C₁-C₄ alkyl;
X, Y and Z are each independently CR₆, CR₇NR₉, N, O or S with the provisos that at least one of X, Y and Z must be O or S, at least one of X, Y and Z must be CR₆ or CR₇R₈, when X or Y is O or S, then Z cannot be O or S and when X and Y are both O and Z is CR₇R₈ the structure must be a, c or e; the ----- configuration represents either a single bond or a double bond with the proviso that when any of X, Y or Z is CR₇R₈, NR₉, O or S, then the ----- configuration represents a single bond and with the further proviso that at least one of the ----- configurations represents a single bond;
R₆, R₇ and R₈ are independently hydrogen, halogen, C₁-C₄ alkoxy or C₁-C₄ alkyl optionally substituted with one hydroxy or one to three halogens, C₁-C₄ alkoxy groups or C₁-C₄ alkylthio groups;
R₉ is hydrogen or C₁-C₄ alkyl optionally substituted with one hydroxy or one to three halogens, C₁-C₄ alkoxy groups or C₁-C₄ alkylthio groups;
Q is hydrogen, halogen, C₁-C₄ alkoxy or C₁-C₄ alkyl optionally substituted with one to three of the following: halogen, C₁-C₄ alkoxy, C₁-C₄ alkylthio or C₂-C₄ alkenyl;
the optical isomers thereof when R₂ and R₃ are not the same or when R₇ and R₈ are not the same;
the tautomers and elastomeric isomers thereof and the acid addition salts thereof except when R₁ is a salt forming cation.

The term halogen designates F, Cl, Br, or I. The term cation, as used in the present specification and claims, designates alkali metals, alkaline earth metals, manganese, copper, iron, zinc, cobalt, lead, silver, nickel, ammonium or organic ammonium. The alkali metals include sodium, potassium and lithium. Among the organic ammonium cations suitable for use in the present invention are monoalkylammonium, dialkyl ammonium, trialkylammonium, tetraalkylammonium, monoalkenylammonium, dialkenylammonium, trialkenylammonium, monoalkynylammonium, dialkynylammonium, monoalkanolammonium, dialkanolammonium, C₅-C₆ cycloalkylammonium, piperidinium, morpholinium, pyrrolidinium, benzylammonium and the like.

Among the o-carboxy-(5-oxo-2-imidazolin-2-yl)benzoheterocycles described in the present invention are o-(2-imidazolin-2-yl)benzofuran carboxylates, o-(2-imidazolin-2-yl)benzothiophene carboxylates, o-(2-imidazolin-2-yl)benzoxazole carboxylates, o-(2-imidazolin-2-yl)benzisoxazole carboxylates, o-(2-imidazolin-2-yl)benzothiazole carboxylates, o-(2-imidazolin-2-yl)benzisothiazole carboxylates, o-(2-imidazolin-2-yl)benzodithiol carboxylates, o-(2-imidazolin2-yl)benzoxathiol carboxylates, o-(2-imidazolin-2-yl)methylenedioxybenzoates and the like.

Preferred compounds of the present invention are those compounds having structure a wherein R₁ is hydrogen, C₁-C₄ alkyl optionally substituted with halogen, C₁-C₃alkoxy, hydroxy, furyl, phenyl or halophenyl, C₂-C₆alkenyl, C₃-C₆cycloalkyl, C₂-C₆alkynyl or a cation; R₂ is methyl; R₃ is isopropyl; B is hydrogen; Z is CR₆ or CR₇R₈ and R₆, R₇, R₈ and Q are each hydrogen.

There is a recognized need in agronomic practice for still more effective herbicidal agents and, especially, effective herbicidal agents which can be used in the presence of important agricultural crops without causing undue injury to said crops. Without adequate control, undesirable plant species can eliminate or reduce the yield of crops, reduce the quality and value of crops and reduce the efficient production and harvest of crops. The herbicidal imidazolinyl benzoheterocycles of the present invention exhibit effective control of a wide variety of undesirable monotyledenous and dicotyledenous plant species and, moreover, demonstrate good selectivity towards important gramineous crops such as wheat and barley.

Herbicidally active imidazolinyl benzoheterocyclic compounds having the structure

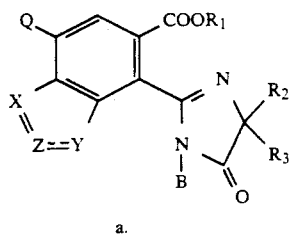

a.

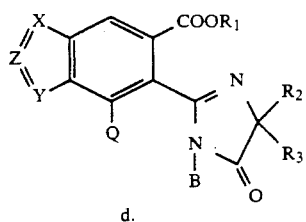

d.

wherein B is hydrogen and $R_1$, $R_2$, $R_3$, X, Y, Z and Q are as described hereinabove can be prepared from their imide nitrile precursors having the structure of formula I.

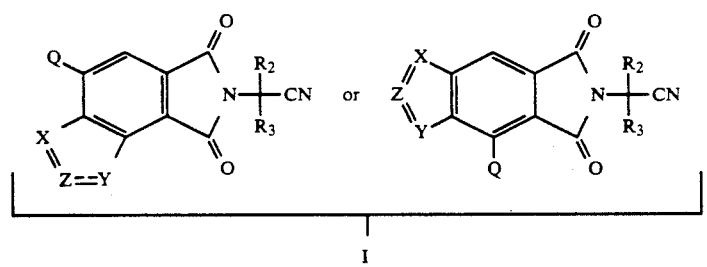

I

The nitrile groups on the formula I compounds can be hydrolyzed in the presence of sulfuric acid to give the corresponding amides and the resultant imide amides ring opened in the presence of an appropriate nucleophile such as an alkali metal alkoxide to give the ester diamide intermediates of formula II and their regioisomers. The formula II ester diamides can be converted to the desired compounds having structure a or b by reaction with phosphorous pentachloride in the presence of a solvent. In the case wherein $R_6$, $R_7$, $R_8$ or $R_9$ contain one or more hydroxy groups, these hydroxy groups are converted to chloro groups by this reaction. The reaction sequence is illustrated in flow diagram I.

FLOW DIAGRAM I

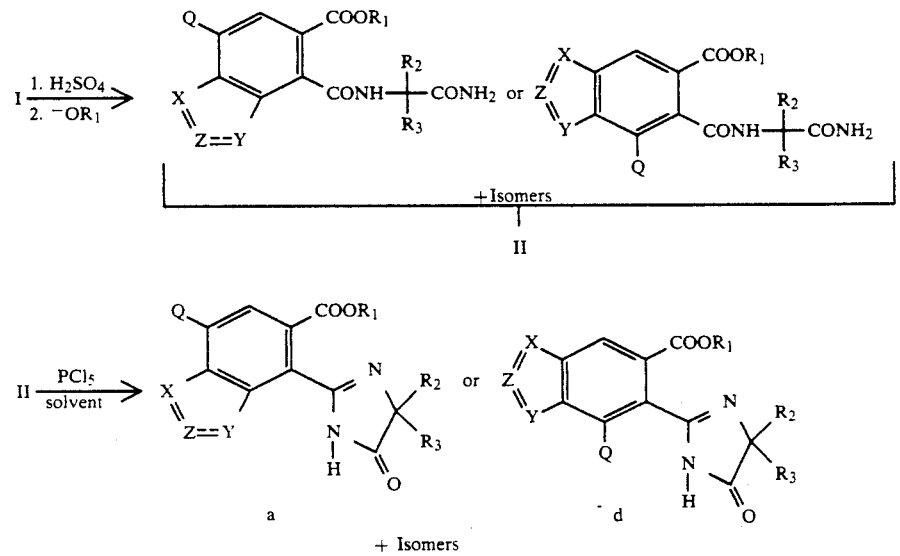

The regioisomers can be separated by standard chromatographic techniques such as reverse phase liquid chromatography.

Alternatively, compounds having structure a or d as described hereinabove and wherein $R_1$ is hydrogen can be prepared in 2 steps by reacting the appropriate phthalic anhydride with an amino amide of formula III in the presence of a base such as triethylamine, and optionally in the presence of a solvent, to obtain the corresponding acid diamide intermediates and their regioisomers and ring closing said intermediates in an aqueous alkali metal base followed by acidification to give the desired o-2(imidazolin-2-yl)benzoheterocyclic carboxylic acids having structure a or d and their regioisomers as shown in flow diagram II.

FLOW DIAGRAM II

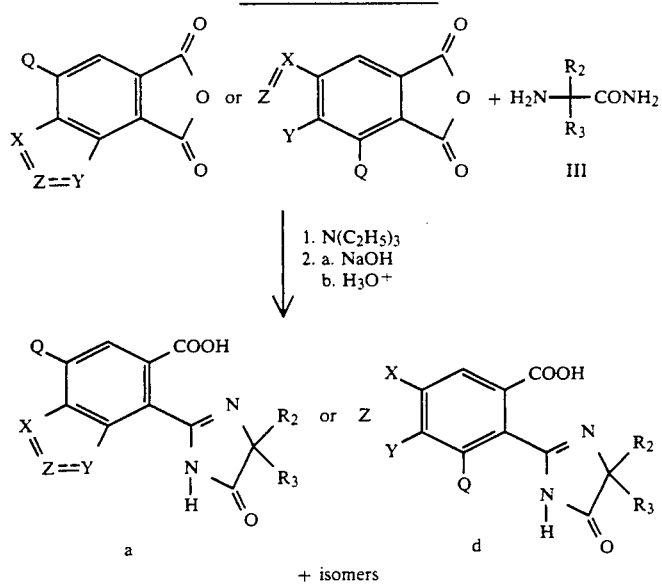

+ isomers

The regioisomers can be separated using standard chromatographic techniques such as reverse phase liquid chromatography.

Compounds of structure a as described above and wherein X is CH, Z is $CR_6$, Y is O or S and B and Q are hydrogen can be prepared by forming the imide nitrile intermediate of formula I via a Diels-Alder reaction of 3-vinylthiophene(or furan) and the appropriately substituted maleimide nitrile of formula IV. Formation of 3-vinylthiophene(or furan) from 3-thiophene(or furano)carboxaldehyde can be achieved via the Wittig reaction. The thus-formed imide nitrile intermediate of formula I can be converted to the desired imidazolinyl fused heterocyclobenzene product of formula V by the reaction sequence described hereinabove and illustrated in flow diagram I. The reaction scheme is shown in flow diagram III.

FLOW DIAGRAM III

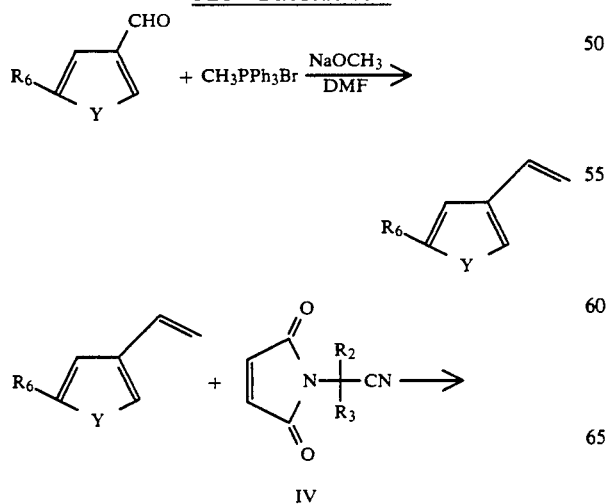

-continued
FLOW DIAGRAM III

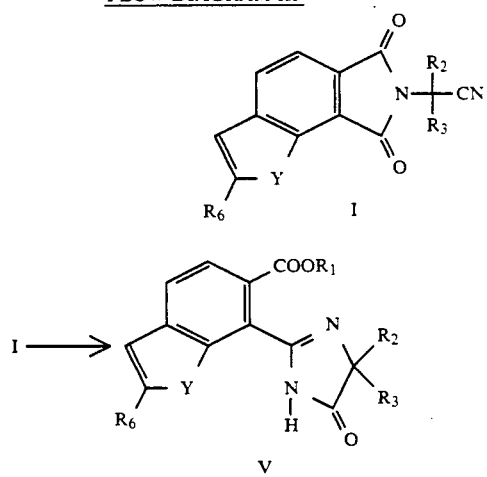

Compounds of structure a wherein Z is O or S, Y is CH, Z is $CR_6$ and B and Q are hydrogen can be prepared in a similar manner. Starting with 2-thiophene(or furano)carboxaldehyde and repeating the reaction sequence in flow diagrams I and III, the imidazolinyl fused heterocyclobenzene compound of formula VI can be prepared.

An alternate route to compounds of structure V wherein $R_6$ is hydrogen consists of the Diels-Alder cycloaddition of 2-methoxyfuran with maleic anhydride to give the oxabicycloheptene intermediate of formula VII, subsequent dehydration and amortization of VII in the presence of trifluoroacetic acid and acetic anhydride to give 3-methoxyphthalic anhydride, formation of the corresponding phthalimide nitrile intermediate of formula VIII using standard procedures, cleavage of the methyl ether of VIII in the presence of boron tribromide to give the corresponding hydroxy derivative having formula IX, alkylation of IX with allyl bromide to give the allyl ether shown as formula X, Claisen rearrangement of X at about 195° C. to give the intermediate of formula XI, ozonolysis of XI to give the mixture of compounds shown as formula XII, treatment of the formula XII mixture with p-toluenesulfonic acid to give the imide nitrile of formula I wherein Y is oxygen and X and Z are CH and reacting the thus-obtained formula I intermediate in the manner described hereinabove in flow diagram I to obtain compounds of formula V wherein Y is oxygen and $R_6$ is hydrogen. The reaction sequence is illustrated in flow diagram IV.

FLOW DIAGRAM IV

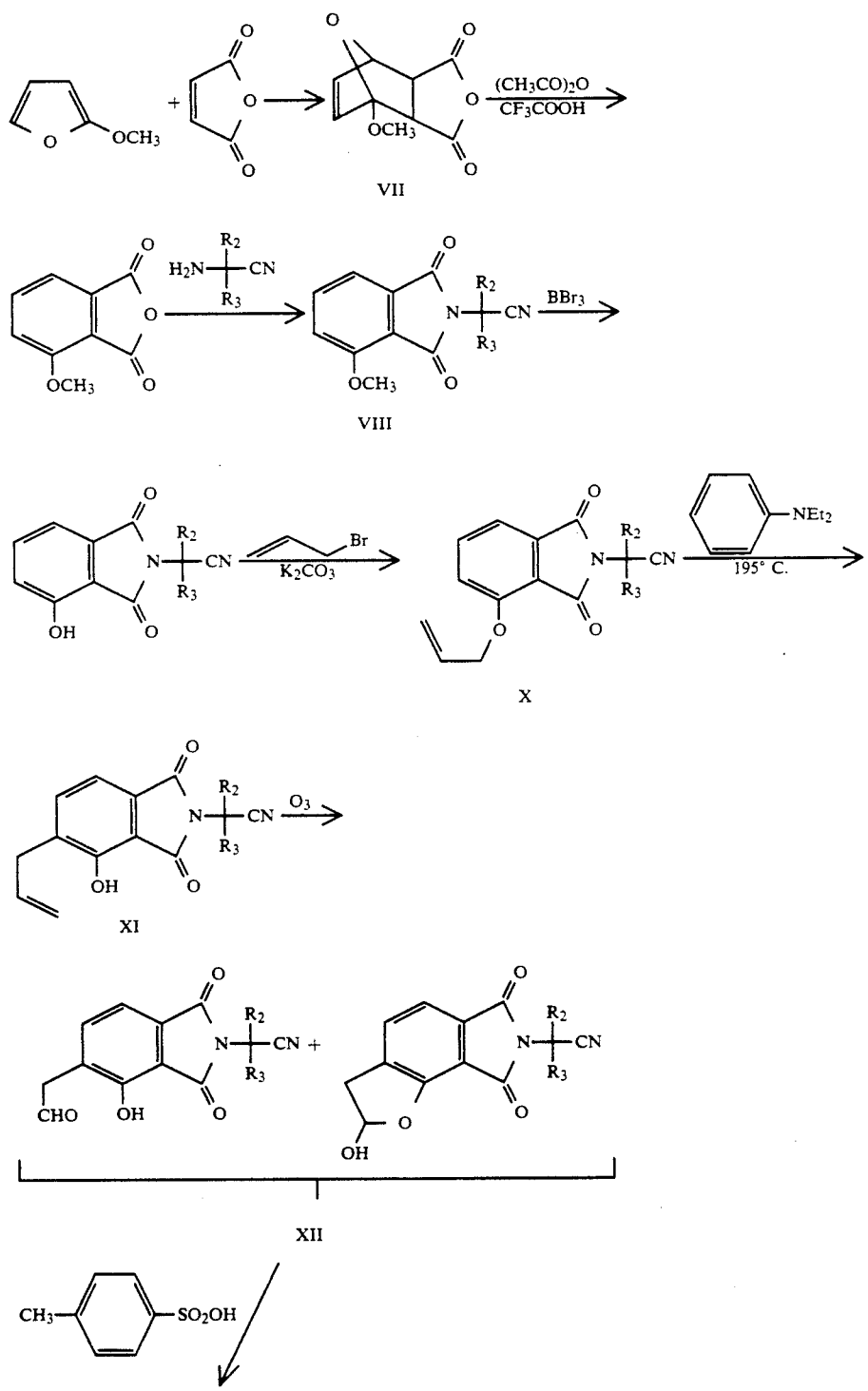

FLOW DIAGRAM IV -continued

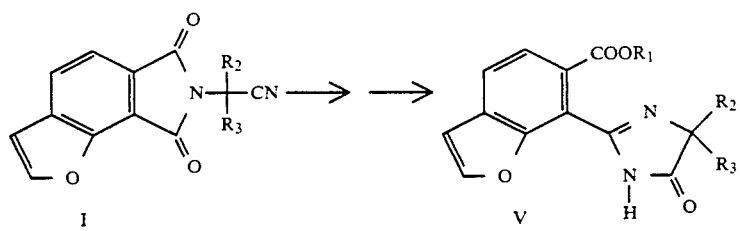

Compounds having structure d wherein X is CH, Y is O, Z is $CR_6$ and $R_1$, $R_6$, B and Q are hydrogen can be prepared from 4-hydroxyphthalate in a similar manner. Alkylation of 4-hydroxyphthalate to form the 4-allyl ether phthalate and Claisen rearrangement of said allyl ether gives a mixture shown as formula XIII which can be ozonized to give the regioisomeric mixture of formula XIV. Ring closure of the hydroxy aldehydes of formula XIV gives the benzofuran diesters of formula XV and XVI. The diesters can be separated using standard chromatographic techniques and the formula XV diester can be converted to the corresponding anhydride of formula XVII by sequential base hydrolysis, acidification and anhydride formation using an acid anhydride. The thus-obtained formula XVII anhydride can then be converted to compounds of formula XVIII using the procedures described hereinabove and illustrated in flow diagram II. The reaction scheme is shown in flow diagram V.

FLOW DIAGRAM V

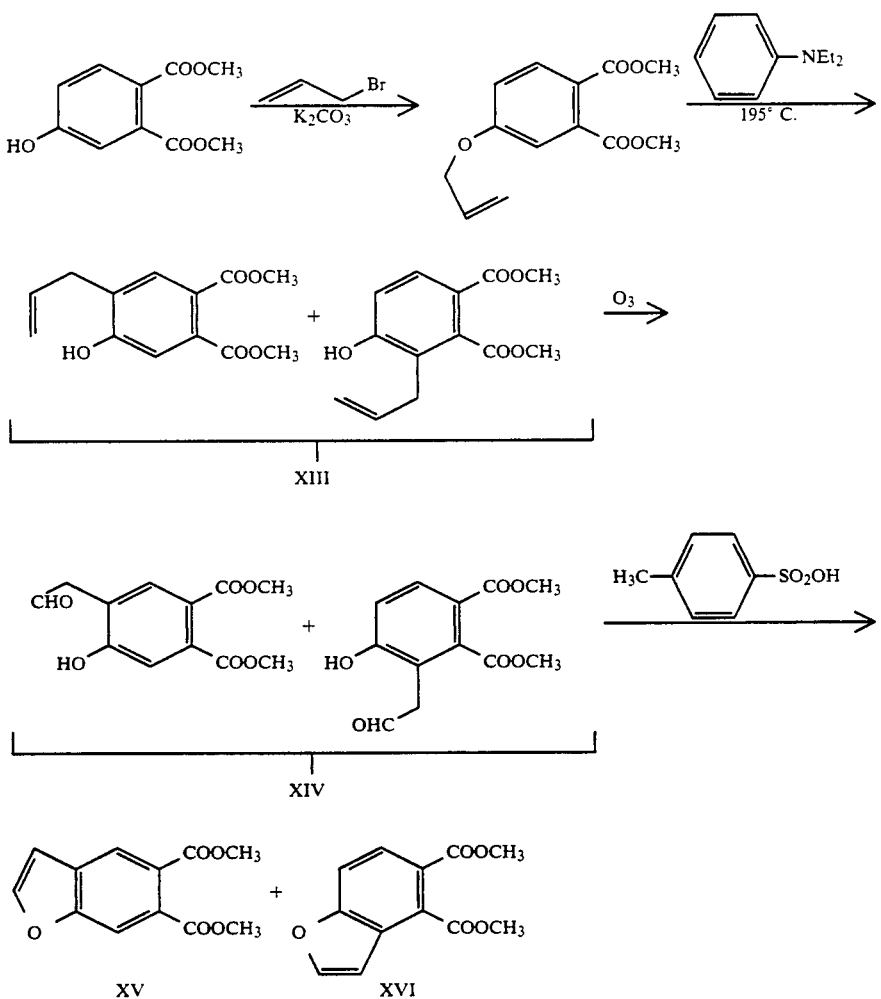

-continued
FLOW DIAGRAM V

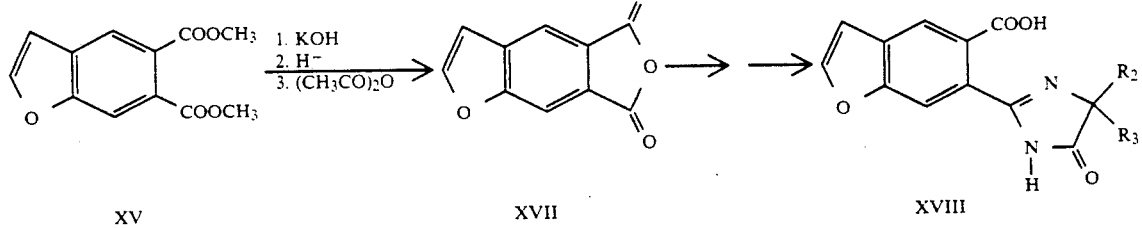

Using the same procedure, intermediate XVI can be converted to imidazolinyl benzoheterocycles of formula VI wherein X is O and $R_1$ and $R_6$ are hydrogen.

Compounds having structure a wherein X and Y are both heteroatoms, Z is $CR_7R_8$ and $R_1$, $R_7$, $R_8$, B and Q are hydrogen can be prepared regiospecificly in the following manner. (For purposes of illustration X and Y are both oxygen.) Metallation and carbonylation of the diethyl amide of pipironylic acid gives the half-acid amide of formula XIX, reaction of XIX with ethyl chloroformate followed by the addition of a formula III amino amide gives the amide diamide of formula XX and base cyclization of XX followed by acid hydrolysis gives the desired imidazolinyl fused heterocyclobenzoic acid of formula XXI. This reaction sequence is illustrated in flow diagram VI.

FLOW DIAGRAM VI

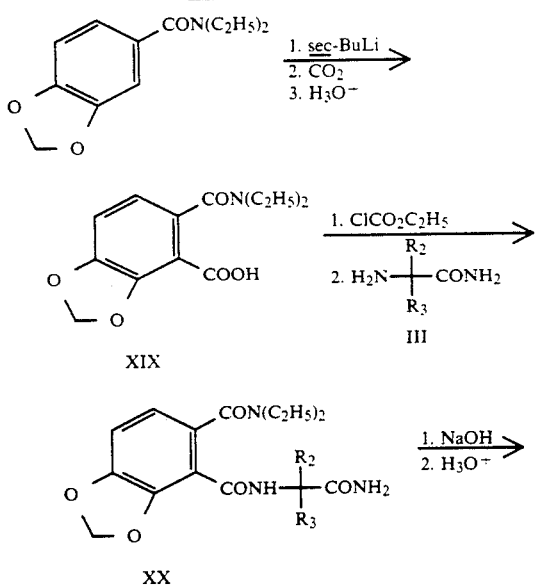

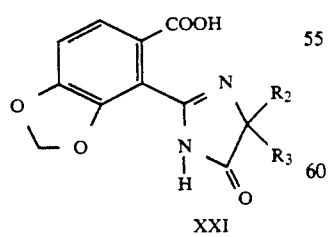

XXI

Compounds having structure c or d can be prepared from compounds having structure a or d wherein $R_1$ is hydrogen by treating said imidazolinyl fused heterocyclobenzoic acids with an excess of an acid anhydride as shown in flow diagram VII. This procedure concommitantly converts any hydroxy groups which may be present as substituents on $R_6$, $R_7$, $R_8$ or $R_9$ to their acetates, which must be then hydrolyzed to liberate the hydroxy groups.

FLOW DIAGRAM VII

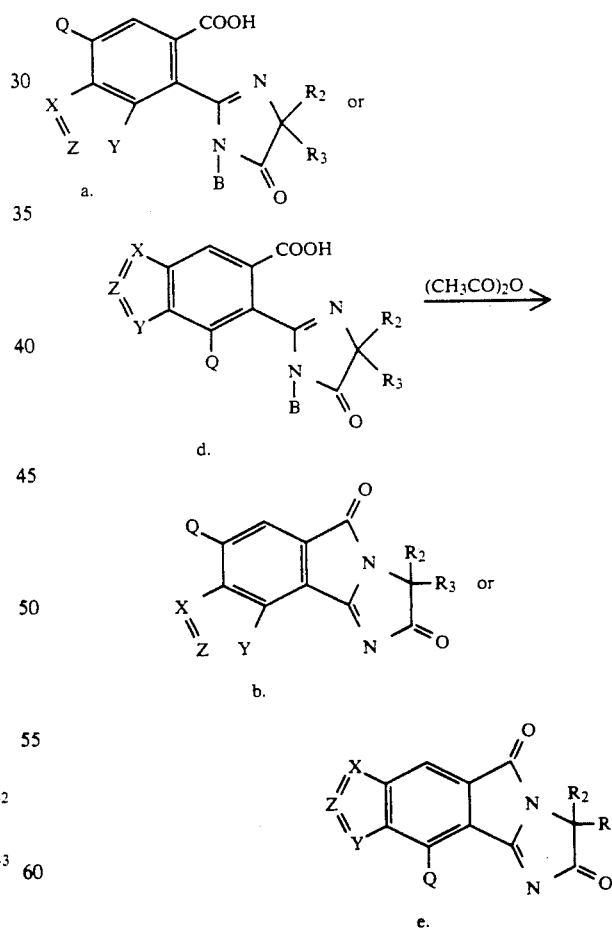

Compounds having structure a or d wherein $R_1$ is other than hydrogen can be prepared from compounds having structure b or e by reacting said compounds with an appropriate nucleophile such as an alkali metal alkoxide as shown in flow diagram VIII.

FLOW DIAGRAM VIII

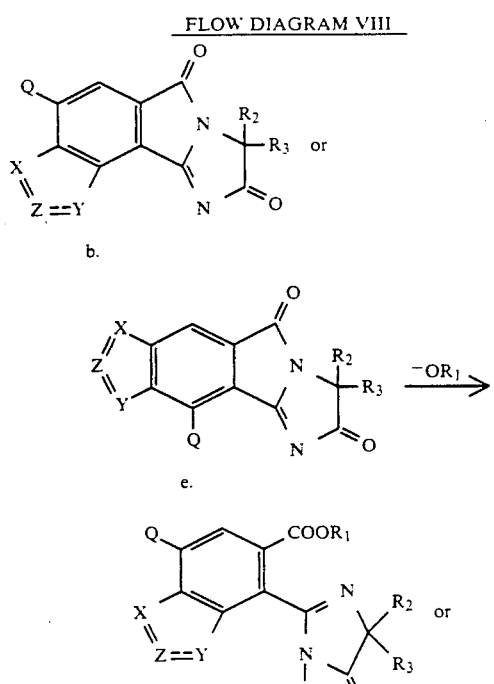

FLOW DIAGRAM IX

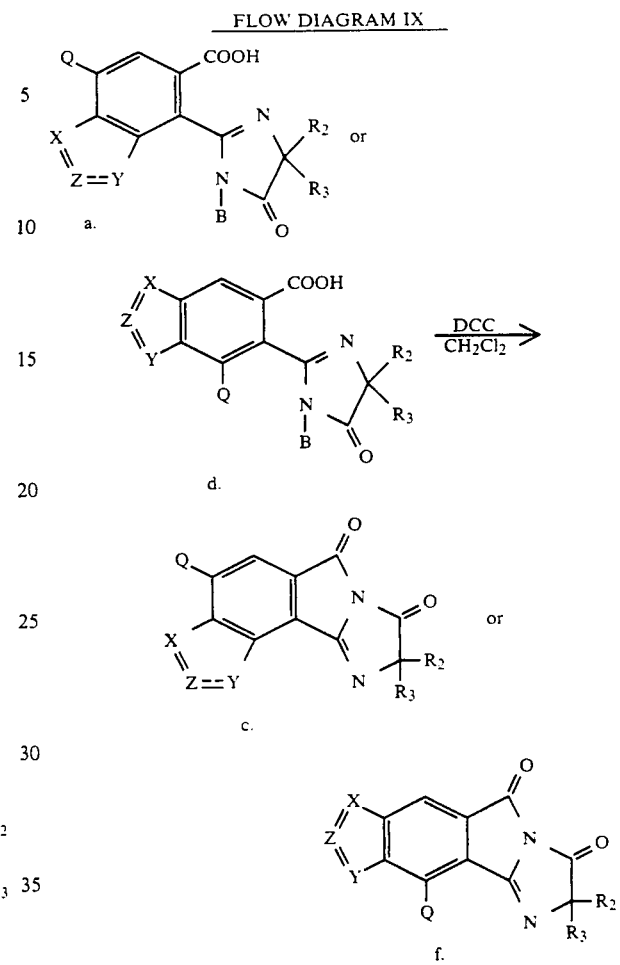

Compounds having structure c or f can be prepared by reacting the o-(2-imidazolin-2-yl)benzoheterocyclic carboxylic acids having structure a or d with dicyclohexylcarbodiimide (DDC) in the presence of a non-protic solvent as shown in flow diagram IX.

Compounds having structure a or d wherein $R_1$ is other than hydrogen or a cation and B is $COR_4$ or $SO_2R_5$ may be prepared by reacting compounds having structure a or d wherein $R_1$ is other than hydrogen or a cation and B is hydrogen with an acyl halide such as an acyl chloride or a sulfonyl halide such as a sulfonyl chloride to obtain the desired products wherein B is $COR_4$ or $SO_2R_5$. The reaction is shown in flow diagram X.

FLOW DIAGRAM X

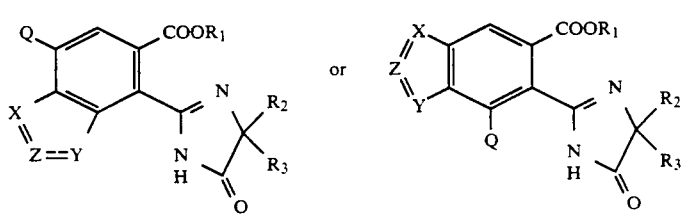

-continued
FLOW DIAGRAM X

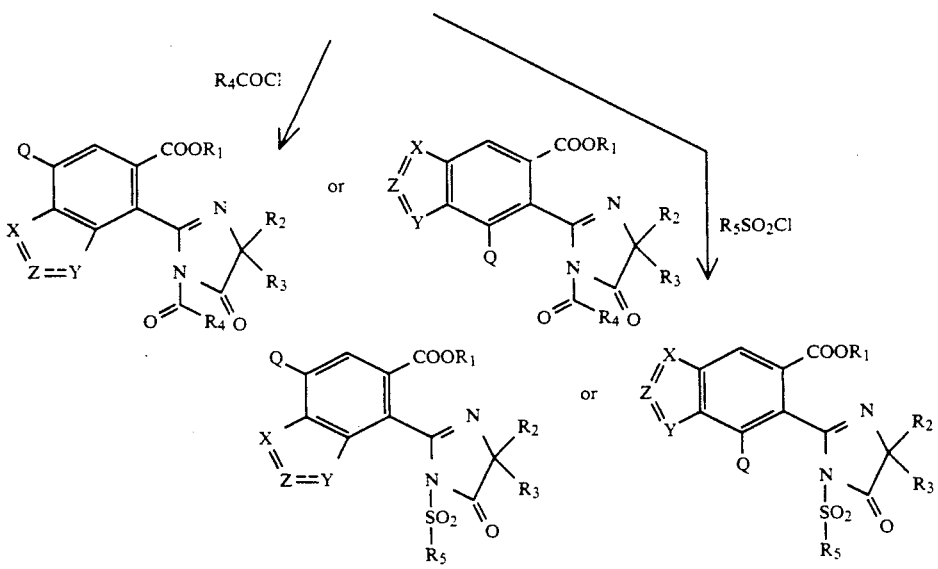

Alternatively, compounds having structure a or d wherein $R_1$ is other than hydrogen or a cation and B is $COR_4$ may be prepared by reacting compounds having structure a or d wherein $R_1$ is other than hydrogen or a cation and B is hydrogen with an acid anhydride of formula $(R_4CO)_2O$.

Other methods for the preparation of the o-carboxy-(2-imidazolin-2-yl)benzoheterocycles and indoloheterocyclic diones of the present invention will become apparent from the examples set forth below.

The imidazolinyl benzoheterocyclic compounds of the present invention are highly effective for controlling a variety of undesirable monocotyledenous plant species such as barnyardgrass, foxtail, purple nutsedge, wild oats, quackgrass and the like and dicotyledenous plant species such as field bindweed, matricaria, morningglory, wild mustard, ragweed, velvetleaf and the like. Control of the above-said plant species can be achieved by applying the compounds of the invention to the foliage of said plants or to soil or water containing seeds or other propagating organs thereof at rates of about 0.032 kg/ha to 8.0 kg/ha.

Surprisingly, it has been found that certain compounds of the invention are well tolerated by gramineous crops such as wheat and barley when said compounds are applied to the foliage of said crops or to soil containing seeds thereof at rates of about 0.032 kg/ha to 1.000 kg/ha. The imidazolinyl benzoheterocyclic compounds may be applied in the form of liquid sprays such as aqueous concentrates, emulsifiable concentrates and the like or as solid formulations such as wettable powders, dispersable granulars, granular formulations and the like.

When the herbicidally active compounds are water soluble, they may simply be dissolved in water and applied as an aqueous spray. Said compounds may also be formulated as emulsifiable concentrates and diluted with water just prior to spray application. A typical emulsifiable concentrate composition can be prepared by dissolving about 5 to 25% by weight of the active compound in about 65 to 90% by weight of N-methylpyrrolidone, isophorone, butyl cellosolve, methyl acetate or the like and dispersing therein about 5 to 10% by weight of a nonionic surfactant such as an alkylphenoxy polyethoxy alcohol.

Wettable powder compositions can be prepared by grinding together about 20 to 45% by weight of a finely divided carrier such as kaolin, bentonite, diatomaceous earth, attapulgite or the like with about 40 to 80% by weight of the herbicidally active compound and about 2 to 5% by weight of a dispersing agent such as sodium lignosulfate and about 2 to 5% by weight of a nonionic surfactant such as an alkyl phenoxy polyethoxy alcohol.

Typical granular products can be prepared by dissolving the active compound in a solvent such as methylene chloride, N-methylpyrrolidone or the like and spraying the resultant solution on a clay carrier such as attapulgite, or kaolin or the like in such a manner so as to produce about 3 to 20% by weight of the active compound and about 80 to 97% by weight of the carrier.

In order to facilitate a further understanding of the invention, the following examples are presented primarily for the purpose of illustrating certain more specific details thereof. The invention is not to be deemed limited thereby except as defined in the claims.

The term kg/ha designates kilograms per hectare. The terms NMR and IR designate nuclear magnetic resonance and infrared, respectively. All parts are parts by weight, unless otherwise noted.

EXAMPLE 1

Preparation of 3-Vinylthiophene

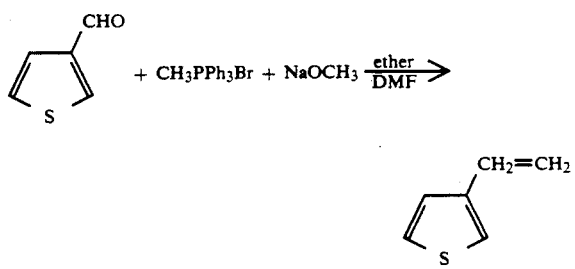

Sodium methoxide (116 g, 0.214 mol) is added to a suspension of methyltriphenylphosphonium bromide (63.6 g, 0.178 mol) in dimethylformamide and ether. A solution of 3-thiophenecarboxaldehyde (20.0 g, 0.178 mol) in ether is added dropwise at 20°–25° C. The resultant mixture is stirred for 20 hours at 30° C. and poured into ice water. The organic layer is saved, the aqueous layer is extracted with ether. The combined organic layers are sequentially washed with water, 30% aqueous sodium bisulfite, saturated sodium bicarbonate, water and brine and dried (MgSO4). Concentration in vacuo affords an orange liquid which is distilled (43°–46° C./15 torr) to afford 3-vinylthiophene as a colorless liquid, 7.90 g 40.3%).

EXAMPLE 2

Preparation of
6,8-Dihydro-α-isopropyl-α-methyl-6,8-dioxo-7H-thieno-[2,3-e]isoindole-7-acetonitrile

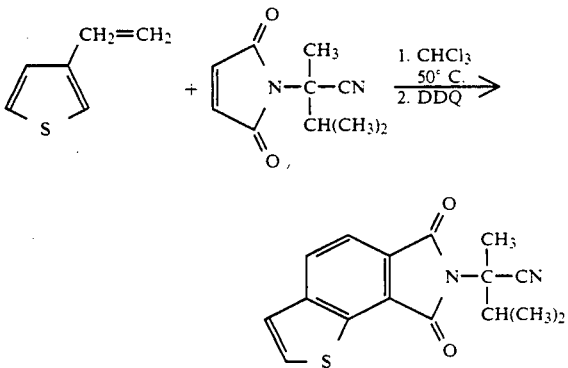

A mixture of 3-vinylthiophene (10.0 g, 0.0908 mol), α-isopropyl-α-methyl-2,5-dioxo-3-pyrroline-1-acetonitrile (18.3 g, 0.0953 mol) and chloroform is stirred at 50° C. for 20 hours and at room temperature for one week. The mixture is concentrated in vacuo to give a yellow oil residue, which is column chromatographed on silica gel using methylene chloride as an eluent to afford a yellow oil. The oil is taken up in dioxane and treated with dichlorodicyano-p-benzoquinone, (17.2 g, 0.0760 mol), stirred for 21 hours at 100° C., cooled to 25° C. and filtered (the filter cake is washed once with benzene). The filtrate is concentrated in vacuo to give an orange semisolid residue. The residue is washed through neutral alumina with methylene chloride:hexanes (1:1) and flash chromatographed on silica gel using hexane:ethyl acetate (4:1) as an eluent to afford the title product as a pale yellow solid, 4.21 g (15.6%), mp 99°–107° C.

EXAMPLE 3

Preparation of 6,8 Dihydro-α-isopropyl-α-methyl-6,8-dioxo-7H-thieno-[2,3-e]isoindole-7-acetamide

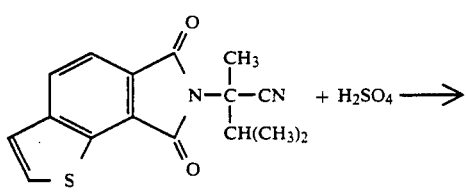

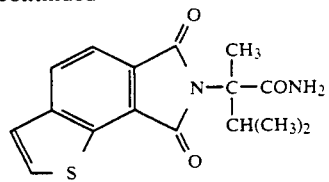

A sample of 6,8-dihydro-α-isopropyl-α-methyl-6,8-dioxo-7H-thieno-[2,3-e]isoindole-7-acetonitrile (1.01 g, 3.35 mmol) is added portionwise to a mixture of water (1.5 mL) and concentrated sulfuric acid (8.5 mL) at −10° C. The reaction mixture is diluted with methylene chloride, stirred for 45 minutes at 5° C., poured onto ice water and extracted with ethyl acetate. The combined extracts are dried (MgSO4) and concentrated in vacuo to give an off-white crystalline residue. Flash chromatography (silica gel, methylene chloride:ethyl acetate eluent) affords the title product as pale-yellow crystals, 0.820 g (77.4%), mp 199°–200° C.

EXAMPLE 4

Preparation of
Methyl-[7-(1-carbamoyl-1,2-dimethylpropyl)carbamoyl]benzo[b]thiophene-6-carboxylate (I),
methyl-[6-[(1-carbamoyl-1,2-dimethylpropyl)]carbamoyl]-benzo[b]thiophene-7-carboxylate (II),
methyl-7-(4-isopropyl-4-methyl-5-oxo-2-imidazolin-2-yl)-6-benzo-[b]thiophenecarboxylate (III) and
methyl-6-(4-isopropyl-4-methyl-5-oxo-2-imidazolin-2-yl)-7-benzo-[b]thiophenecarboxylate (IV)

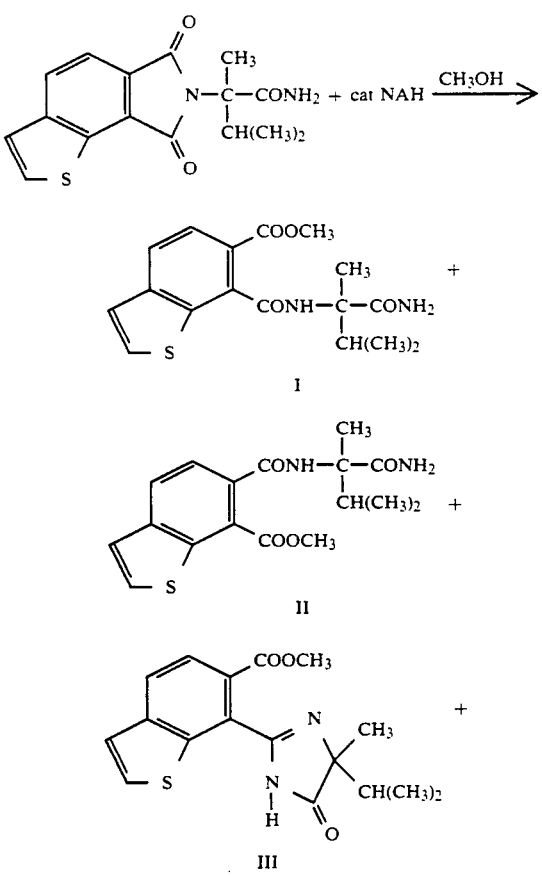

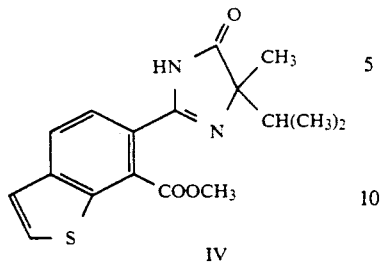

A catalytic amount of sodium hydride (60% oil dispersion) is added to a solution of 6,8-dihydro-α-isopropyl-α-methyl-6,8-dioxo-7H-thieno-[2,3-e]isoindole-7-acetamide (4.20 g, 13.3 mmol) in methanol such that the resulting pH is 10–11. The reaction mixture is stirred overnight at room temperature, acidified to pH 5 with acetic acid and filtered. The filtrate is concentrated in vacuo to give a tan solid residue which is flash chromatographed (silica gel, gradient elution with 80% methylene chloride:ethyl acetate to 5% methanol:methylene chloride) to afford the title products as the following 6 fractions:

1. $R_f$ 0.47, white crystals, (IV) (0.300 g), mp 162°–163° C.
2. $R_f$ 0.36, colorless solid (III) 0.540 g), mp 143°–147° C.
3. $R_f$ 0.30–0.36, colorless syrup (crude III) (0.29 g).
4. $R_f$ 0.17, white crystals, (I) (0.22 g), mp 85°–91° C.
5. $R_f$ 0.17–0.14, off-white crystals (2.55 g), NMR indicates an 86:14 mixture of (I) and (II).
6. $R_f$ 0.14, pale yellow crystals (II) (0.30 g), mp 84°–93° C.

The title products are identified by NMR and IR spectral analyses.

EXAMPLE 5

Preparation of
Methyl-7-(4-isopropyl-4-methyl-5-oxo-2-imidazolin-2-yl)-6-benzo[b]thiophenecarboxylate (I) and
methyl-6-(4-isopropyl-4-methyl-5-oxo-2-imidazolin-2-yl) -7-benzo[b]thiophenecarboxylate (II), 9:1 mixture

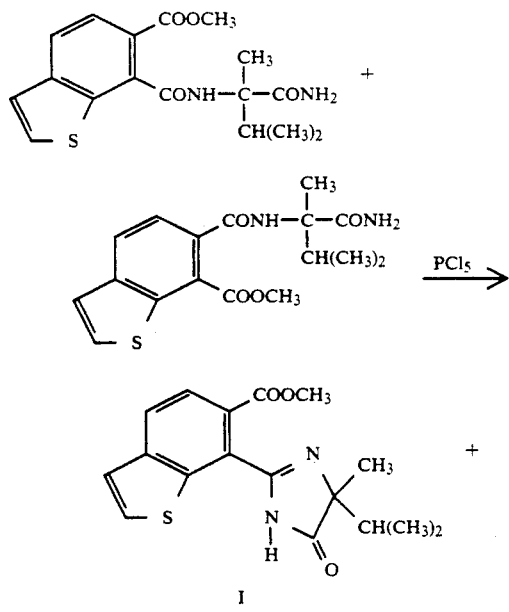

An 86:14 mixture of methyl-7(and 6)-[(1-carbamoyl-1,2-dimethylpropyl) carbamoyl]benzo[b]thiophene-6(and 7)-carboxylate (2.55 g, 7.37 mmol) in toluene:chloroform (50% v/v) is added dropwise to a suspension of phosphorus pentachloride (3.05 g, 14.6 mmol) in toluene at 0° C. under a nitrogen atmosphere. The reaction mixture is stirred for 21 hours at ambient temperature, poured onto ice water and extracted with ethyl acetate. The organic extract is washed sequentially with water, saturated sodium bicarbonate and brine and dried (MgSO₄). Concentration in vacuo affords a yellow solid residue which is flash chromatographed (silica gel, 15% ethyl acetate:methylene chloride eluent) to yield the title product mixture as a white solid (0.43 g) 17.8% yield, mp 143°–147° C., NMR spectral analysis indicates the product contains 90–95% of compound I.

EXAMPLE 6

Preparation of
7-(4-Isopropyl-4-methyl-5-oxo-2-imidazolin 2-yl) benzo[b]thiophene-6-carboxylic acid and
6-(4-isopropyl-4-methyl-5-oxo-2-imidazolin-2-yl) benzo[b]thiophene-7-carboxylic acid, 1:1 mixture

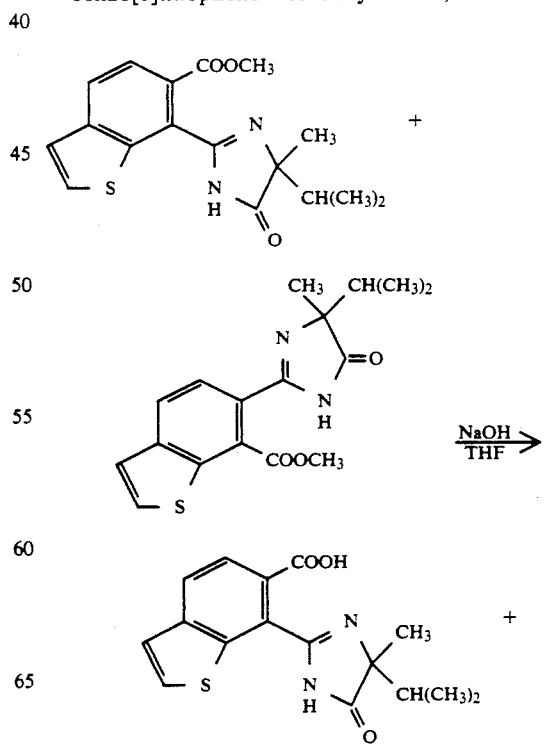

-continued

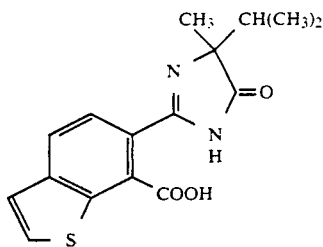

A solution of an 87:13 mixture of methyl-7-(and 6)-(4-isopropyl-4-methyl-5-oxo-2-imidazolin-2-yl)-benzo[b]-thiophene-6(and 7)carboxylate (0.440 g, 1.26 mmol) in tetrahydrofuran is treated with aqueous sodium hydroxide (1.06 mL, 2.65 mmol, 2.5 M), stirred for 20 hours at 41° C., cooled to room temperature, concentrated in vacuo, diluted with water, acidified to pH 1-2 with concentrated sulfuric acid and extracted with ethyl acetate. The organic extracts are combined, dried (MGSO4) and concentrated in vacuo to afford an off-white solid. Recrystallization from acetonitrile:hexanes (9:1) affords the title product mixture as an off-white solid, 0.100 g (26.2%), mp 197°-201° C. Identified by NMR spectral analysis.

EXAMPLE 7

Preparation of 7-(4-Isopropyl-4-methyl-5-oxo-2imidazolin-2-yl)-6-benzo[b]thiophene carboxylic acid

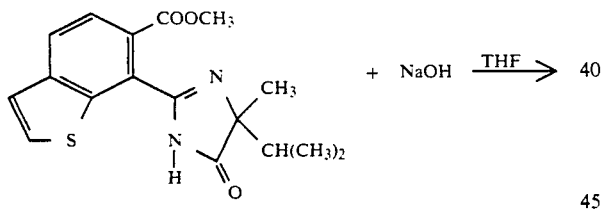

A mixture of methyl 7-(4-isopropyl-4methyl-5-oxo-2-imidazolin-2-yl)-6-benzo [b]thiophene carboxylate (90% pure, 0.420 g, 1.20 mmol), aqueous sodium hydroxide (1.01 mL, 2.53 mmol) and tetrahydrofuran (15 mL) is stirred overnight at 40°-45° C., cooled to room temperature, concentrated in vacuo, and acidified to pH 1-2 with concentrated sulfuric acid. Extraction with ethyl acetate, drying (MgSO4), concentration and recrystallization from acetonitrile:hexanes (9:1) affords the title product as an off-white solid, 0.22 g, mp 200°-202° C.

EXAMPLE 8

Preparation of Endo- and exo-1-methoxy-7-oxabicyclo-[2.2.1]hept-5-ene-2,3-dicarboxylic anhydride

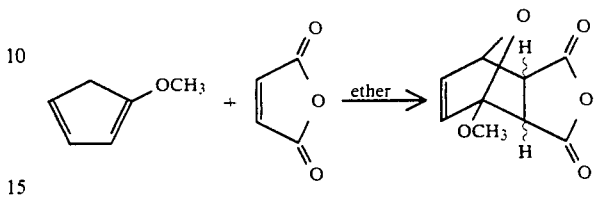

A solution of 2-methoxyfuran (65.0 g, 0.662 mol) in ether is added dropwise to a solution of maleic anhydride (71.4 g, 0.729 mol) in ether, resulting in an exotherm to reflux temperature. The reaction mixture is stirred for 4 hours at reflux temperature, cooled to room temperature and stirred overnight. Filtration affords the title product as white crystals, 126.6 g (97.5%), mp 108°-110° C.

EXAMPLE 9

Preparation of 3-Methoxyphtahalic anhydride

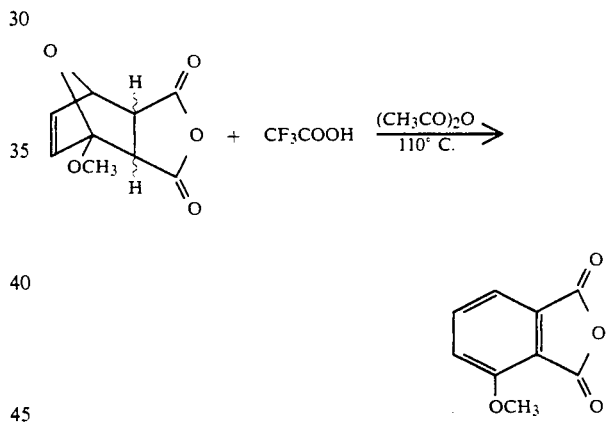

A mixture of endo- and exo-1-methoxy-7-oxabicyclo[2.2.1]hept-5-ene-2,3-dicarb oxylic anhydride (23.4 g, 0.119 mol), acetic anhydride and trifluoroacetic acid is stirred for 1.5 hours at 110° C., cooled to room temperature and stirred overnight. Filtration affords the title product as off-white crystals, 9.03 g, mp 159°-160° C.

EXAMPLE 10

Preparation of α-Isopropyl-4-methoxy-α-methyl-1,3-dioxo-2-isoindolineacetonitrile

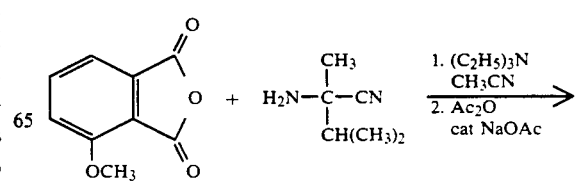

-continued

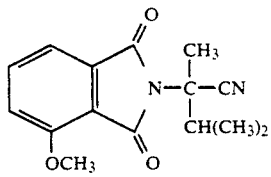

To a stirred mixture of 3-methoxyphthalic anhydride (17.3 g, 0.0972 mol) in acetonitrile is added a mixture of α-methylvalinnitrile (13.1 mL, 0.107 mol), triethylamine (13.5 mL, 0.0972 mol) and acetonitrile over a 20 minute period. The reaction mixture is stirred for 17 hours at room temperature, concentrated in vacuo, treated with acetic anhydride (170 mL) and sodium acetate (1.00 g) and stirred for 3 hours at reflux temperature, removed heat source and stirred overnight at ambient temperatures. Concentration of the reaction mixture in vacuo affords a viscous black oil residue which is filtered through neutral alumina (400 g) with methylene chloride as eluent. The resultant methylene chloride filtrate is washed with 2N HCl followed by brine, dried (MgSO₄), and concentrated in vacuo to afford a pale-yellow crystalline residue. Recrystallization from ether gives the title product as yellowish-white crystals, 13.3 g (50.2%), mp 118-°121° C.

EXAMPLE 11

Preparation of 4-Hydroxy-α-isopropyl-α-methyl-1,3-dioxo-2-isoindolineacetonitrile

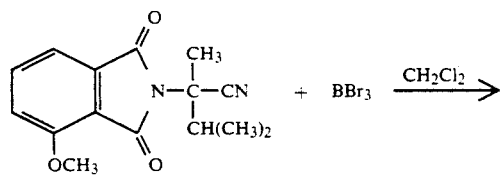

Boron tribromide (109 mL, 0.109 mol, 1.0M in methylene chloride) is added dropwise to a solution of α-isopropyl-4-methoxy-2-methyl-1,3-dioxo-2-isoindolineacetonitrile (9.25 g, 0.034 mol) in methylene chloride at −75° C. The mixture is stirred for 3 days at ambient temperatures, poured slowly onto cold water and diluted with methylene chloride. The organic layer is separated, dried (MgSO₄) and concentrated in vacuo to give a pale-yellow solid. Recrystallization from methylene chloride/hexane yields the title product as a light tan solid, 8.68 g (89.0%), mp 110°-111° C.

EXAMPLE 12

Preparation of 4-Allyloxy-α-isopropyl-α-methyl-1,3-dioxo-2-isoindolineacetonitrile

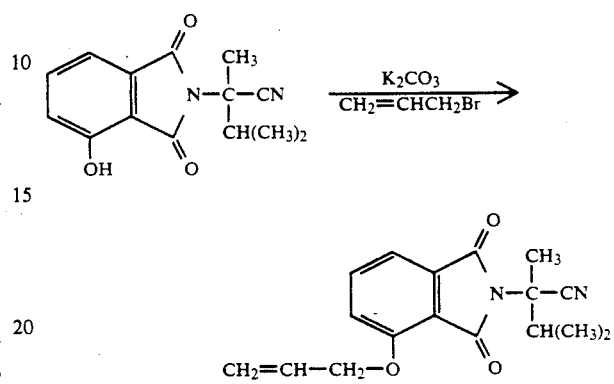

A mixture of 4-hydroxy-α-isopropyl-α-methyl-1,3-dioxo-2-isoindolineacetonitrile (25.5 g, 0.099 mol), potassium carbonate (75.0 g, 0.543 mol) and acetone is stirred for 4 hours at reflux temperature under a nitrogen atmosphere, cooled to room temperature and treated with allyl bromide (34.1 mL, 0.395 mol). The reaction mixture is stirred overnight at reflux temperature, cooled to room temperature and filtered. The filtrate is concentrated in vacuo, diluted with ether, washed with brine, dried (MgSO₄) and concentrated in vacuo to afford the title product as a yellow-orange semi-solid, 26.9 g (91.5% crude yield). The sample is purified by flash chromatography (silica gel, CH₂Cl₂) to afford a colorless solid, mp 54°-58° C.

EXAMPLE 13

Preparation of 5-Allyl-4-hydroxy-α-isopropyl-α-methyl-3-dioxo-2-isoindolineacetonitrile (I) and 4-Allyl-7-hydroxy-α-isopropyl-α-methyl-1,3-dioxo-2-isoindolineacetonitrile (II)

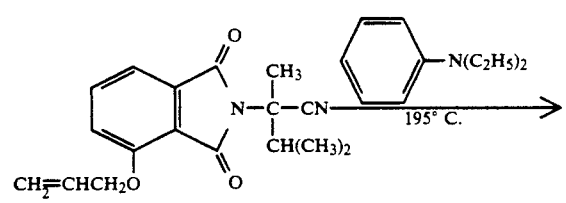

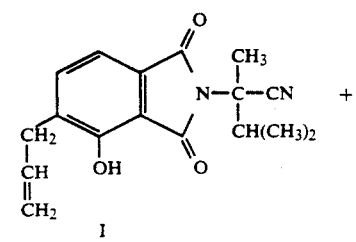

-continued

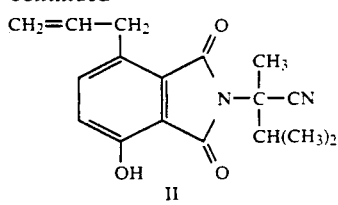

II

A mixture of 4-allyloxy-α-isopropyl-α-methyl-1,3-dioxo-2-isoindolineacetonitrile (16.4 g, 0.055 mol) and diethylaniline (20 mL) is stirred for 4 hours at 195° C., cooled to room temperature, diluted with ether and washed with 2N HCl (4 portions), followed by brine. The organic layer is dried (MgSO$_4$) and concentrated in vacuo to give a tan oil residue, which is flash chromatographed (silica gel, hexanes:ethylacetate eluent) to afford 2 isomers. The isomer of higher R$_f$ is I, and is obtained as a viscous yellow oil, 8.90 g (54.2%). The isomer of lower R$_f$ II, and is obtained as a viscous yellow oil, 1.09 g (6.64%).

EXAMPLE 14

Preparation of 5-Formylmethyl-4-hydroxy-α-isopropyl-α-methyl-1,3-dioxo-2-isoindolineacetonitrile (I) and 2,3-dihydro-α-isopropyl-α-methyl-6,8-dioxo-7e,uns/H/-furo-[2,3-e]isoindolineacetonitrile, (II) 1:1 mixture

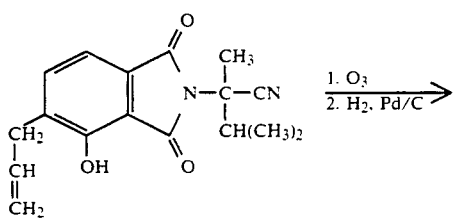

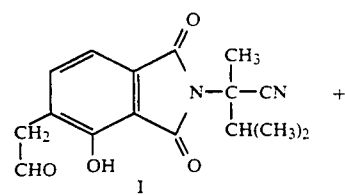
I

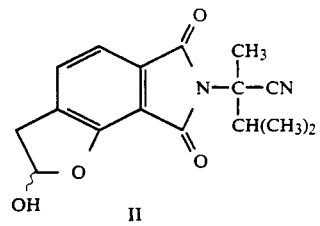
II

Ozone is bubbled into a solution of 5-allyl-4-hydroxy-α-isopropyl-° -methyl-1,3-dioxo-2-isoindoline-acetonitrile (1.06 g, 3.55 mmol) and methylene chloride at −5° C. using a Welsbach ozone generator with compressed air as carrier gas. After 15 minutes, the reaction is purged with air, paladium on carbon (10%, mg) and calcium carbonate (0.150 g) are added and hydrogen is introduced at one atmosphere until uptake ceases. The reaction mixture is filtered through celite, and the filtrate is concentrated in vacuo to give the title product mixture as a pale-yellow solid, 1.18 g, identified by NMR spectral analysis. This mixture is used in Example 15.

EXAMPLE 15

Preparation of α-Isopropyl-α-methyl-6,8-dioxo-7Hfuro-[2,3-e]isoindoline-7-acetonitrile

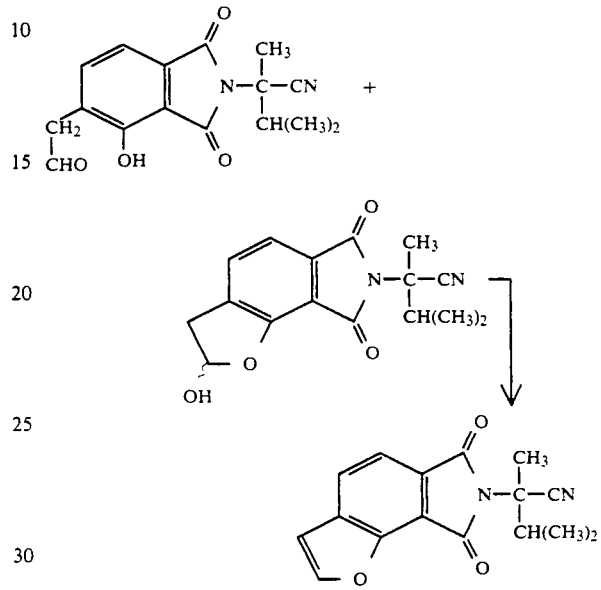

The crude mixture obtained in Example 14, above, (3.30 g, 11.0 mmol), para-toluenesulfonic acid (2.09 g, 11.0 mmol) and benzene is stirred for 3 hours at reflux temperature with azeotropic removal of water and stirred for 24 hours at room temperature. The reaction mixture is diluted with ethyl acetate and washed with saturated sodium bicarbonate, water and brine. Drying (MgSO$_4$) and concentration in vacuo followed by flash chromatography (silica gel, methylen chloride) affords the title product as a yellow oil, 0.610 g (19.7%), identified by NMR spectral analysis.

EXAMPLE 16

Preparation of α-Isopropyl-α-methyl-6,8-dioxo-7H-furo[2,3-e]isoindoline-7-acetamide

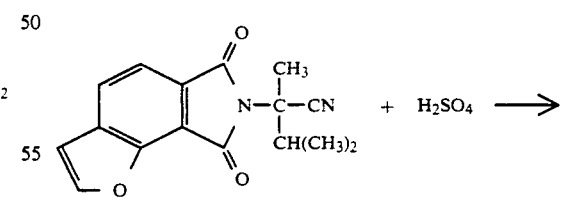

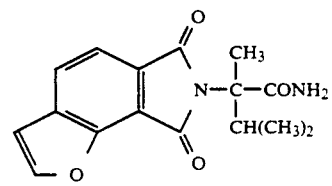

To a stirred mixture of α-isopropyl-α-methyl-6,8-dioxo-7H-furo [2,3-e]isoindoline-7-acetonitrile (0.580 g, 2.05 mmol) in methylene chloride is added a mix of concentrated sulfuric acid (3 mL) and water (0.5 mL) dropwise at 0° C. The red reaction mixture is stirred for 30 minutes at 0° C., 2 hours at ambient temperature, poured into ice water and extracted with ethyl acetate. The organic extract is dried (MgSO4) and concentrated in vacuo to afford the title product as a pale-yellow solid, 0.570 g (92.5%), identified by NMR and mass spectral analyses.

EXAMPLE 17

Preparation of Methyl 7( and 6) -[(1carbamoyl-1,2-dimethylpropyl)carbamoyl]-6( and 7) -benzofurancarbonxylate

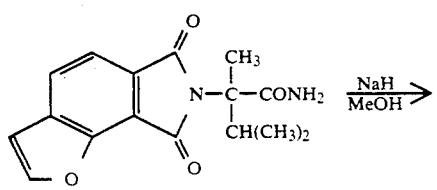

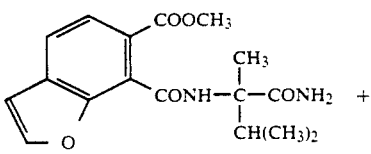

major

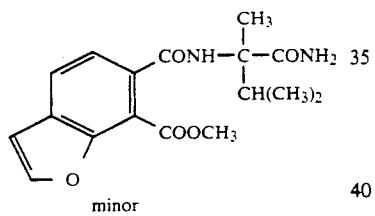

minor

A catalytic amount of sodium hydride (60% oil dispersion) is added to a mixture of α-isopropyl-α-methyl-6,8-dioxo-7H-furo [2,3-e]isoindoline-7-acetamide (0.550 g, 1.83 mmol) in methanol to pH 10. The reaction mixture is stirred for 16 hours at room temperature, treated with acetic acid to pH 5 and concentrated in vacuo to give a pale yellow solid residue. The residue is taken up in methylene chloride, washed with water and brine, dried, (MgSO4) and concentrated in vacuo to afford the title product mixture as a yellow solid, 0.450 g (73.9%). This material is used as is in Example 18 below.

EXAMPLE 18

Preparation of Methyl 7(and 6)-(4-isopropyl-4-methyl-5-oxo-2-imidazolin-2-yl)-6(and 7)-benzofurancarboxylate

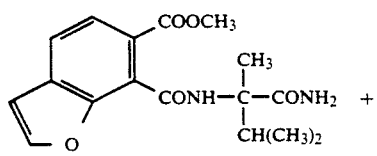

-continued

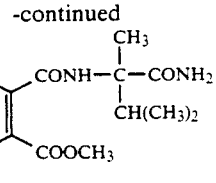

PCl5 $\xrightarrow{\text{toluene}}{\text{CHCl}_3}$

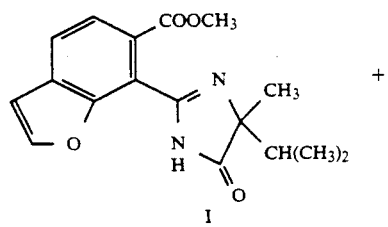

I

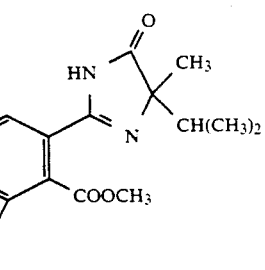

II

A solution of the mixture obtained in Example 17, (0.450 g, 1.36 mmol) in chloroform is added dropwise wise to a suspension of phosphorus pentachloride (0.560 g, 2.72 mmol) in toluene at 3° C. under a nitgrogen atmosphere. The reaction mixture is stirred 22 hours at ambient temperatures and diluted with ethyl acetate, ice and saturated sodium bicarbonate. The organic layer is separated, washed with brine, dried (MgSO4), and concentrated in vacuo to afford a yellow gum residue. Flash chromatography (silica gel, gradient elution with methylene chloride to 10% methanol:methylene chloride) affords the title product mixture as yellow crystals, 0.080 g (18.7%), mp 168°–172° C. Analysis by NMR spectroscopy indicates the product mixture consists of 87% I and 13% II.

EXAMPLE 19

Preparation of 1,3-Benzodioxole-5-carbonoyl chloride

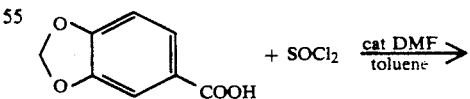

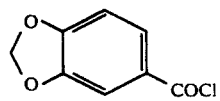

A mixture of piperonylic acid (100 g, 0.601 mol), thionyl chloride (45.9 mL, 0.602 mol), dimethylformamide (0.50 mL) and toluene is stirred for 2 hours at reflux temperature, cooled and concentrated in vacuo

EXAMPLE 20

Preparation of N,N-Diethylpiperonylamide

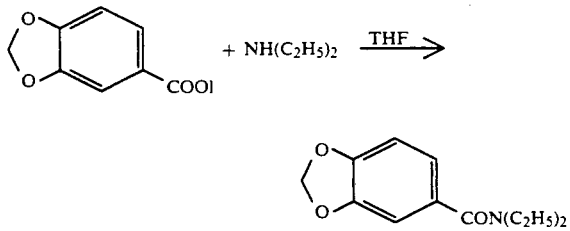

A solution of diethylamine (56.2 mL, 0.543 mol) in tetrahydrofuran is added dropwise to a solution of piperonyl chloride (33.4 g, 0.181 mol) in tetrahydrofuran at 0° C. The reaction mixture is stirred for 10 minutes and filtered through diatomaceous earth. The filtrate is concentrated in vacuo to give a solid residue which is recrystalized from ether to afford the title product, 36.7 g (91.8%).

EXAMPLE 21

Preparation of Dimethyl 3,4-(methylenedioxy)phthalate

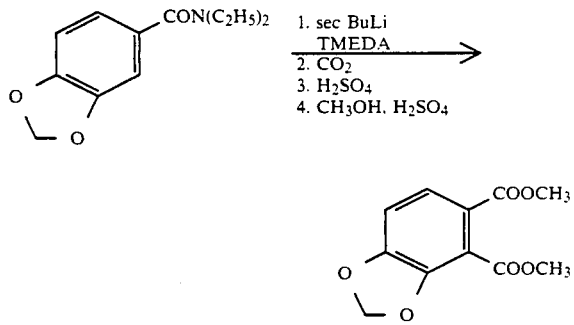

A solution of N,N-diethylpiperonylamide (47.2 g, 0.213 mol) in tetrahydrofuran is added dropwise to a mixture of tetramethylethylenediamine (TMEDA, 32.2 mL, 0.213 mol), sec-butyllithium (213 mL, 0.213 mol, 1M in cyclohexane) and tetrahydrofuran at −70° C. to −50° C. After 10 minutes at −70° C., carbon dioxide is bubbled in for 30 minutes. The reaction mixture is allowed to warm to room temperature and concentrated in vacuo to a dark oil residue. The residue is treated with ethyl acetate, saturated ammonium chloride, and concentrated sulfuric acid is added to pH 1 with ice bath cooling. The resultant mixture is continuously extracted with ethyl acetate for 16 hours and the organic phase is concentrated in vacuo to afford a residue. Methanol and concentrated sulfuric acid is added to the thus-obtained residue and the mixture is heated to reflux temperature. The reaction mixture is cooled, concentrated in vacuo and the residue is chromatographed (silica gel, ether eluent) and recrystallized from ethyl acetate to afford the title product as a white solid, mp 57°-59° C.

EXAMPLE 22

Preparation of N,N-Diethyl-5,6-(methylenedioxy)phthalamic acid

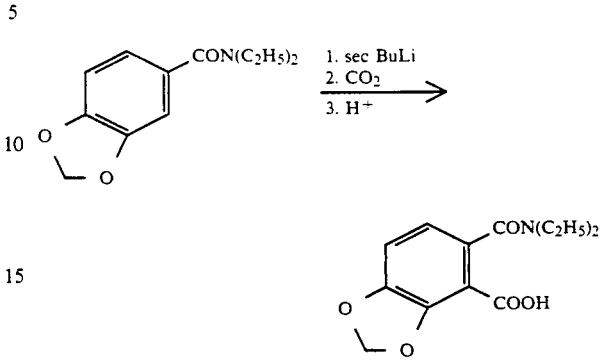

A solution of N,N-diethylpiperonylamide 10.0 g, 45.0 mmol) in tetrahydrofuran is added dropwise at −65° C. to −55° C. to a mixture of sec-Butyllithium (500 mL, 50.0 mmol, 1M in cyclohexane) in tetrahydrofuran under a nitrogen atmosphere. The reaction mixture is poured over tetrahydrofuran saturated with dry ice, allowed to warm to 0° C., treated slowly with water and acidified to pH 3 with concentrated sulfuric acid. The tetrahydrofuran is removed in vacuo and the aqueous residue is extracted with ethyl acetate. The organic extract is dried (MgSO$_4$) and concentrated in vacuo to a yellow-orange gum, NMR and mass spectrographic analysis show it to be a mixture of starting material and the title product. The above aqueous layer is acidified further to pH 2, extracted with ethyl acetate, and the organic extract is dried (MgSO$_4$) and concentrated in vacuo to yield the title product as a yellow foam, 4.00 g (33.6%) identified by NMR spectral analysis.

EXAMPLE 23

Preparation of 3,4-methylenedioxy)phthalic anhydride

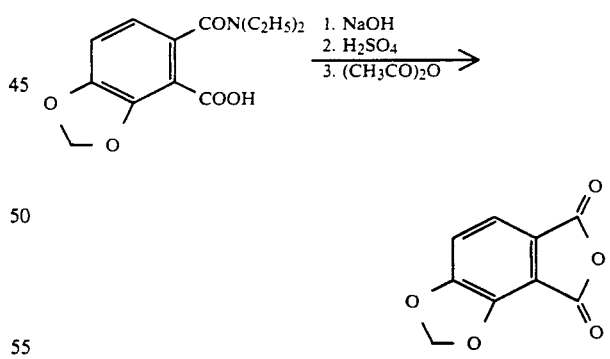

A mixture of N,N-diethyl-5,6-(methylenedioxy)phthalamic acid (7.7 mL, 0.150 mol) and 2N sodium hydroxide (75 mL, 0.150 mol) is heated on a steam bath for 4 hours, allowed to stand overnight at room temperature, cooled to 10° C., acidified to pH 2 with concentrated sulfuric acid and extracted with ethyl acetate. The organic extract is dried (MgSO$_4$) and concentrated in vacuo to a yellow solid, which is taken up in acetic anhydride, stirred overnight at reflux temperature and concentrated in vacuo to give a brown solid residue. The residue is washed with ether and filtered to afford the title product, 10.6 g (82.8%), mp 160°-162° C.

EXAMPLE 24

Preparation of
Methyl-2-(4-isopropyl-4-methyl-5-oxo-2-imidazolin-2-yl)-3,4-(methylenediozy)benzoate

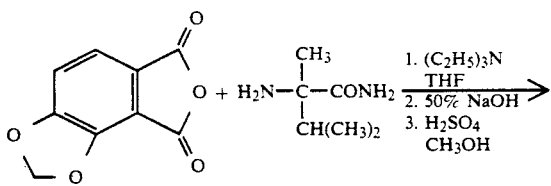

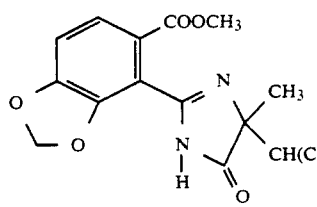

A solution of 3,4-(methylenedioxy)phthalic anhydride (20.0 g, 0.104 mol) in tetrahydrofuran is treated with α-methylvalinamide (14.9 g, 0.114 mol), followed by triethylamine (16.0 mL, 0.114 mol), stirred for 16 hours at room temperature and concentrated in vacuo to give a residue. The residue is diluted with tetrahydrofuran and 50% aqueous sodium hydroxide, heated on a steam bath for 3 hours, acidified with concentrated sulfuric acid and continuously extracted for 16 hours with ethyl acetate. The organic extract is concentrated in vacuo to give a solid which is taken up in methanol and concentrated sulfuric acid, stirred for 2 hours at reflux temperature, treated with additional sulfuric acid, stirred for 6 hours at reflux temperature, cooled and neutralized with solid sodium bicarbonate. Continuous extraction overnight with ethyl acetate and concentration of the organic phase in vacuo affords a solid. Recrystallization from ethyl acetate affords the title product, 10.0 g (30.2%), mp 175°-179° C.

EXAMPLE 25

Preparation of
2-(4-Isopropyl-4-methyl-5-oxo-2-imidazolin-2-yl)-3,4-(methylenedioxy)benzoic acid

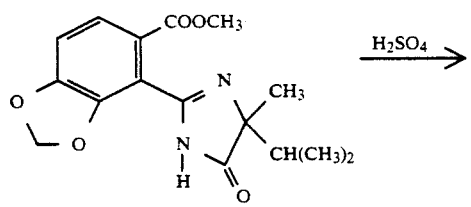

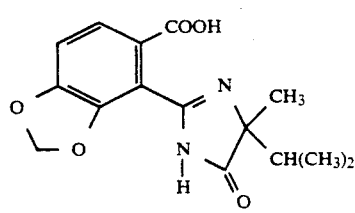

Methyl 2-(4-isopropyl-4-methyl-5-oxo-2-imidazolin-2-yl)-3,4-(methylenedioxy)benzoate (6.00 g, 16.9 mmol) is added to 7.5N sulfuric (100 mL), stirred for 15 hours at reflux temperature, cooled to 0° C. and treated with 6N sodium hydroxide to pH 4. The resultant mixture is continuously extracted with ethyl acetate overnight, and the organic layer is concentrated in vacuo to afford the title product as a white solid, 3.40 g (59.1%), mp 172°-176° C.

EXAMPLE 26

Preparation of
N-(1-Carbamoyl-1,2-dimethylpropyl)-3,4-methylenedioxy) phthalamic acid and
N-(1-carbamoyl-1,2-dimethylpropyl)-5,6-(methylenedioxy)phthalamic acid, 7:3 mixture with triethylamine

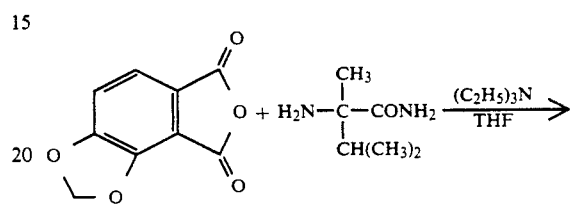

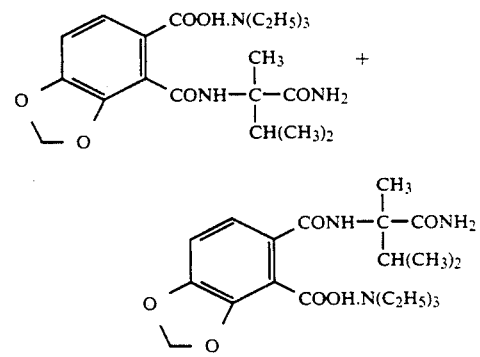

A solution of 3,4-(methylenedioxy)phthalic anhydride (10.6 g, 55.0 mmol) in tetrahydrofuran at room temperature is treated with α-methylvalinamide (7.20 g, 55.0 mmol) and triethylamine (8.50 mL, 61.0 mmol), stirred for 72 hours at room temperature and filtered to afford the title product mixture as a white solid, 18.7 g (77.6%), mp 140°-155° C. The product mixture ratio is determined by NMR spectral analysis.

EXAMPLE 27

Preparation of
2-(4-Isopropyl-4-methyl-5-oxo-2-imidazolin-2-yl)-3,4-(methylenedioxy) benzoic acid (I) and
6-(4-Isopropyl-4-methyl-5-oxo-2-imidazolin-2-yl)-3,4-methylenedioxy)benzoic acid (II)

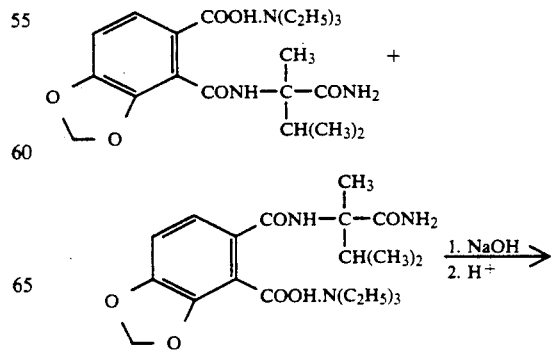

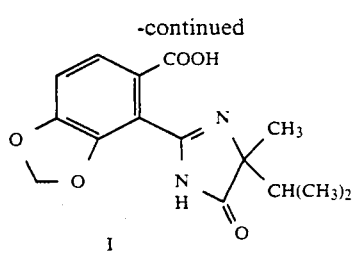

A mixture of N-(1-carbamoyl-1,2-dimethylpropyl)-3,4(and 5,6)-(methylenedioxy)phthalamic acid 18.7 g, 42.7 mmol), 6N sodium hydroxide (50 mL, 300 mmol) and dioxane is heated on a steam bath for 3.5 hours and cooled to room temperature. The aqueous phase is separated, cooled to 10° C., acidified to pH 3 with concentrated sulfuric acid and extracted with ethyl acetate. The organic extract is allowed to stand at room temperature overnight, affording compound II as colorless needles, 2.37 g (16.9%), mp 136°–138° C. The mother liquor is concentrated in vacuo to a pale-yellow foam, which is recrystallized from ethyl acetate to afford compound I as a white solid, 6.38 g (47.6%), mp 198°–202° C.

EXAMPLE 28

Preparation of N'-(1-Carbamoyl-1,2-dimethylpropyl)-N,N-diethyl-3,4-(methylenedioxy)phthalamide A solution of N,N-diethyl-5,6-)methylenedioxy)phthalamic acid (3.00 g, 11.0 mmol) in tetrahydrofuran, under nitrogen at room temperature is treated with ethyl chloroformate (1.10 mL, 11.0 mmol), cooled to 10° C., treated with triethylamine (1.70 mL, 12.0 mmol), stirred for 30 minutes at 10° C., treated dropwise with a solution of α-methylvalinamide (1.43 g, 11.0 mmol) in tetrahydrofuran, stirred overnight at ambient temperatures, treated with water and concentrated in vacuo. The aqueous residue is extracted with ethyl acetate; the extracts are combined, washed with brine and saturated sodium bicarbonate, dried (MgSO₄), and concentrated in vacuo to afford the title product as an amber foam 3.10 g (74.7%), identified by NMR and mass spectral analysis.

EXAMPLE 29

Preparation of N,N-Diethyl-2-(4-isopropyl-4-methyl-5-oxo-2-imidazolin-2-yl) piperonylamide A mixture of N'-(1-carbamoyl-1,2-dimethylpropyl)-N,N-diethyl-3,4-(methylenedioxy) phthalamide (3.10 g, 8.20 mmol), dioxane and 1.93N sodium hydroxide (21.2 mL, 41.1 mmol) is heated on a steam bath for 2.5 hours and concentrated in vacuo. The residue is treated with water, acidified to pH 2 with concentrated sulfuric acid and filtered to yield the title compound as an off-white solid, 1.85 g (62.9%), mp 205°–211° C.

EXAMPLE 30

Preparation of 2-(4-Isopropyl-4-methyl-5-oxo-2-imidazolin-2-yl)-3,4-(methylenedioxy) benzoic acid A mixture of N,N-diethyl-2-(4-isopropyl-4-methyl-5-oxo-2-imidazolin-2-yl) piperonylamide (0.500 g, 1.39 mmol), dioxane and concentrated hydrochloric acid is heated on a steam bath for 16 hours. The dioxane is removed in vacuo and the residue taken up in water and treated with 50% sodium hydroxide to pH 3–4. Filtration gives the title product as a white solid, 0.400 g (94.6%), mp 220° C. (dec).

EXAMPLE 31

Preparation of 9-Isopropyl-9-methyl-6H-1,3-dioxolo[4,5-g]imidazo[2,1-a]isoindole-6,8(9H)dione

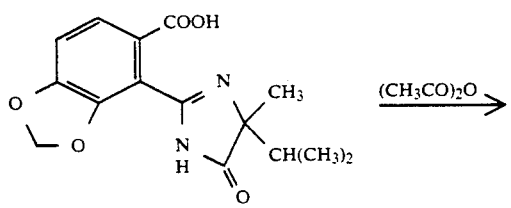

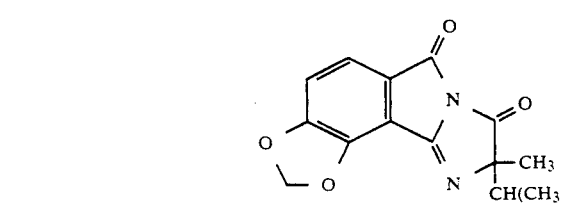

A mixture of 2-(4-isopropyl-4-methyl-5-oxo-2-imidazolin-2-yl)-3,4-(methylenedioxy) benzoic acid (3.40 g, 11.2 mmol) and acetic anhydride (20 mL, 0.211 mol) is stirred overnight at reflux temperature. Concentration in vacuo and recrystallized from ethyl acetate to yield the title product as a white solid, 1.50 g (46.9%), mp 237°–242° C., identified by NMR spectral analysis.

EXAMPLE 32

Preparation of 8-Isopropyl-8-methyl-6-H-1,3-dioxolo[4,5-g]imidazo[2,1-a]isoindole-6,9(8H)dione

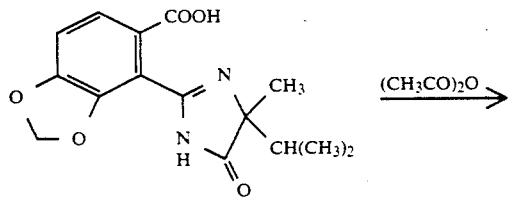

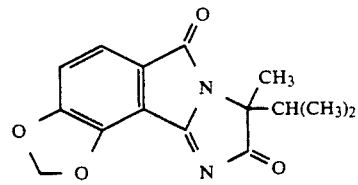

A mixture of 2-(4-isopropyl-4-methyl-5-oxo-2-imidazolin-2-yl)-3,4-(methylenedioxy) benzoic acid (4.11 g, 13.5 mmol) and acetic anhydride (100 mL, 1.06 mol) is stirred overnight at reflux temperature and concentrated in vacuo to give a residue which is chased twice with toluene to give a pale yellow solid. Recrystallization from ethyl acetate affords the title product as a pale yellow solid, 2.77 g (69.9%), mp 158°–160° C., identified by NMR spectral analysis.

EXAMPLE 33

Preparation of Furfuryl 2-(4-isopropyl-4-methyl)-5-oxo-2-imidazolin-2-yl)piperonylate and 2-propynyl [2-(4-isopropyl-4-methyl-5-oxo-2-imidazolin-2-yl)]piperonylate

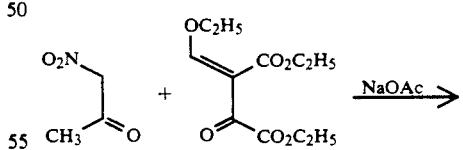

R = CH₂— (furyl)

R = CH₂C≡CH

A stirred mixture of 8-isopropyl-8-methyl-6-H-1,3-dioxolo-[4,5-g]imidazo[2,1α]-isoindole-6,9-(8H)-dione, 4 equivalents of furfuryl alcohol and toluene is treated with sodium hydride (60% oil dispersion) to pH 10, stirred overnight at room temperature, treated with acetic acid to pH 5 and concentrated in vacuo to give a residue which is dispersed in water and methylene chloride. The organic phase is dried (MgSO₄) and concentrated in vacuo to give a gum residue which is triturated in ether to afford the title furfuryl ester product as a white solid, 2.00 g (87.7%), mp 161°–163° C.

Using essentially the same procedure and substituting propargyl alcohol affords the title propargyl ester product as a white solid, 1.33 g (55.4%), mp 161°–163° C.

EXAMPLE 34

Preparation of Diethyl 4-hydroxy-5-nitrophthalate

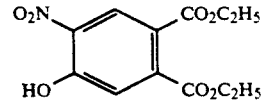

A stirred mixture of nitro-2-propanone (63.50 g, 0.616 mol), (ethoxymethylene)oxalacetic acid, diethyl ester (151.1 g, 0.616 mol) and ethanol at 5° C. under a nitrogen atmosphere is treated with sodium acetate (101.1 g, 1.23 mol), stirred overnight at room temperature, and concentrated in vacuo. The resultant residue is chromatographed (silica gel, 1% ethyl acetate:hexanes eluent). The chromatographed material is taken up in ethyl acetate and extracted with an equivalent of aqueous sodium hydroxide. The basic layer is acidified to pH 2-3 with concentrated hydrochloric acid and extracted with ethyl acetate. The organic extract is dried and concentrated in vacuo to give the title product as a yellow oil, 16.0 g, identified by NMR and mass spectral analyses.

EXAMPLE 35

Preparation of Diethyl 4-amino-5-hydroxyphthalate

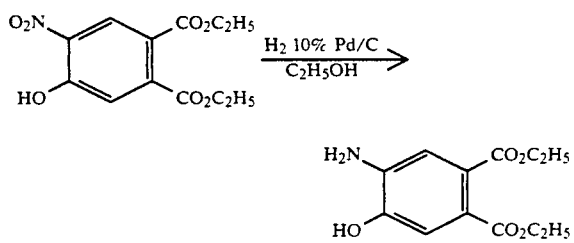

A solution of diethyl-4-hydroxy-5-nitrophthalate (16.0 g, 56.7 mmol) in ethanol is treated with 10% palladium on carbon (1.6 g) and shaken overnight at room temperature on a Parr hydrogenator. After evacuation of hydrogen, the reaction mixture is filtered through diatomaceous earth. The filtrate is concentrated in vacuo to afford the title product as a yellow oil, 14.3 g (100%) identified by NMR spectral analysis.

EXAMPLE 36

Preparation of Diethyl 2-methyl-5,6-benzoxazoledicarboxylate

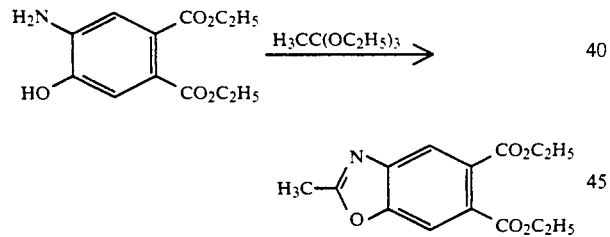

A mixture of diethyl-4-amino-5-hydroxyphthalate (4.00 g, 15.8 mmol) and triethylorthoacetate (29.0 mL, 158 mmol) is stirred for 2 hours at reflux temperature, cooled to room temperature and diluted with hexanes. Silica gel chromatography (gradient elution:hexanes to (2:1) hexanes:ethyl acetate) followed by recrystallization from 1% ethyl acetate:-hexanes affords the title product as an off-white crystalline solid, 3.54 g (80.8%), identified by NMR, IR and mass spectral analyses.

EXAMPLE 37

Preparation of 2-Methyl-5,6-benzoxazoledicarboxylic acid

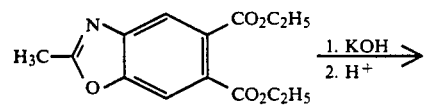

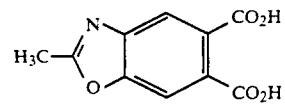

A mixture of diethyl 2-methyl-5,6benzoxazoledicarbodylate (2.42 g, 8.72 mmol), water, ethanol and potassium hydroxide (2.53 g, 45.1 mmol) is stirred overnight at reflux temperatures and cooled to room temperature. The ethanol is removed in vacuo. The aqueous residue is acidified to pH 2-3 with hydrochloric acid and concentrated in vacuo. The resultant residue is slurried in acetone, filtered and the filtrate is concentrated in vacuo to give the title product as a tan solid, 2.10 g (71.0%) identified by NMR, IR, and mass spectral analyses.

EXAMPLE 38

Preparation of 5(or 6)-(4-Isopropyl 4-methyl 5-oxo-2-imidazol-2-yl)-2-methyl -6(or 5)-benzoxazolecarboxylic acid and 4-isopropyl-2,4-dimethyl-2-imidazolin-5one

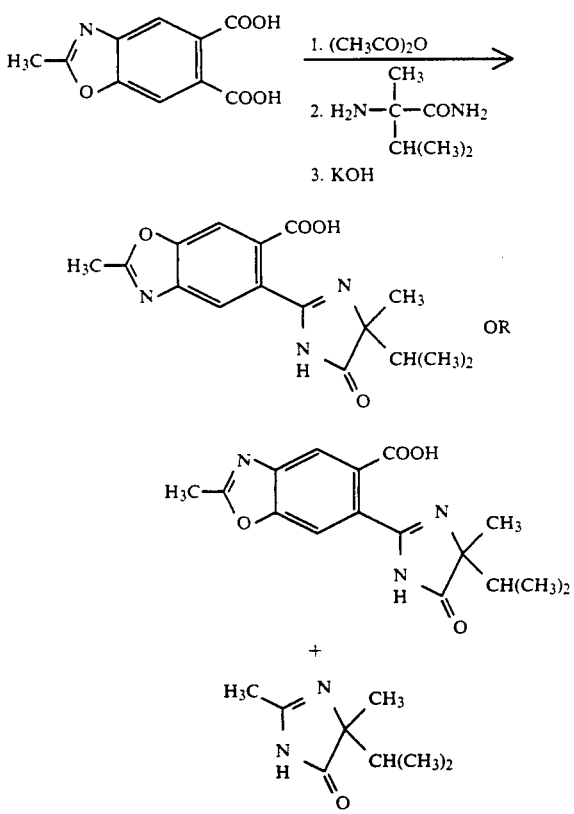

A suspension of 2-methyl-5,6-benzoxazoldicarboxylic acid (2.10 g, 9.50 mmol) in acetic anhydride is heated at 50° C. for 5 hours, and at 76° C. for 16 hours. The reaction mixture is cooled, concentrated in vacuo to give a gummy solid residue, which is washed with ether. The ether washes are combined and evaporated to afford a pale-orange solid (1.26 g) which is treated with a solution of α-methylvalinamide (0.845 g, 6.50 mmol) in tetrahydrofuran at room temperature. The reaction mixture is stirred for 16 hours, concentrated in vacuo and triturated under ether to afford a tan solid (2.20 g).

The solid is treated with potassium hydroxide (i 88 g, 33.5 mmol) and water and the mixture heated at 60° C. for 2 hours, and at 80° C. for 2 hours, then cooled, acidified to pH 3-4 with concentrated hydrochloric acid and concentrated in vacuo. The resultant residue is flash chromatographed (silica gel, methanol-ethyl acetate eluent) to afford the title product mixture as a light yellow solid, identified by NMR and mass spectral analyses.

EXAMPLE 39

Preparation of Dimethyl 4-hydroxy-5-nitrophthalate and Dimethyl 4-hydroxy-3-nitrophthalate

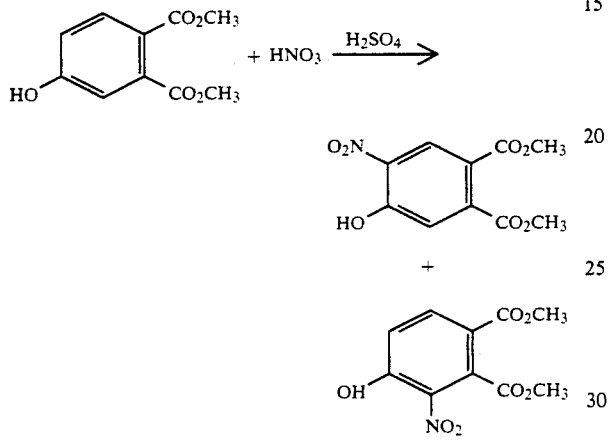

A mixture of dimethyl 4-hydroxyphthalate (25.0 g, 0.119 mol) and concentrated sulfuric acid at 0°–5° C., is treated dropwise with nitric acid (90%, 6.10 mL, 0.142 mol), stirred for 10 minutes, poured into ice water and extracted with ethyl acetate. The combined organic extracts are dried (MgSO$_4$) and concentrated in vacuo to give the title product mixture as a viscous yellow oil, 29.7 g (98.0%), identified by NMR spectral analysis. Flash chromatography (silical gel, 2% ethyl acetate/methylene chloride) of the mixture gives dimethyl 4-hydroxy-5-nitrophthalate as a yellow solid 3.70 g, mp 82°–85° C. and dimethyl 3-nitro-4-hydroxyphthalate as a pale yellow solid, 3.80 g, mp 108°–111° C.

EXAMPLE 40

Preparation of Dimethyl 3-amino-4-hydroxyphthalate

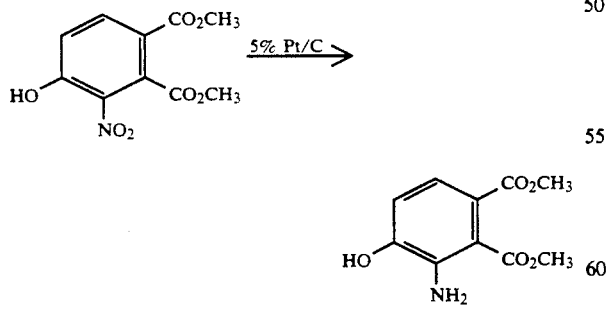

A mixture of dimethyl 3-nitro-4-hydroxyphthalate (28.9 g, 0.113 mol), ethanol and 5% platinum on carbon (2.80 g, 50% aqueous) is shaken on a Parr hydrogenator under hydrogen for 1.75 hours at room temperature. The reaction mixture is filtered through diatomaceous earth and the filtrate is concentrated in vacuo to give a pale green solid residue. Chromatography (silica gel, ethyl acetate:methylene chloride eluent) affords the title product as a pale yellow solid, 3.69 g, mp 112°–113° C., identified by NMR and IR spectral analyses.

EXAMPLE 41

Preparation of Dimethyl 2-methyl-5,6-benzoxazoledicarboxylate

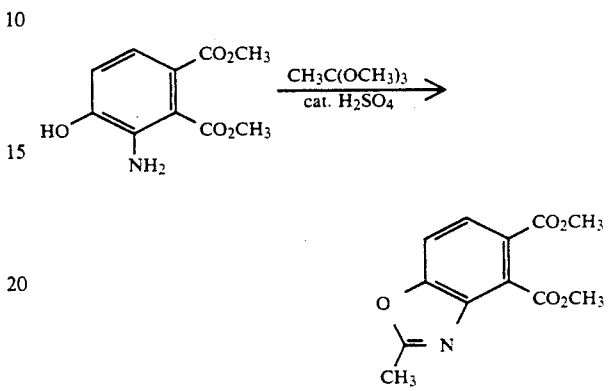

A mixture of dimethyl 3-amino-4-hydroxyphthalate (17.0 g, 0.0755 mol), trimethylorthoformate (13.5 mL, 0.106 mol) and concentrated sulfuric acid is heated with removal of methanol by short path distillation in an oil bath (117°–135° C.) for 45 minutes and cooled to room temperature. The remaining orange solid is flash chromatographed (silica gel, hexanes:ethyl acetate eluent) to afford the title compound as a tan solid, 14.9 g (79.2%), mp 121°–124° C., identified by NMR spectroscopy.

EXAMPLE 42

Preparation of 3-Acetamido-4-hydroxyphthalic acid (I) and 2-methyl-4,5-benzoxazoledicarboxylic acid (II), 4:1 mixture

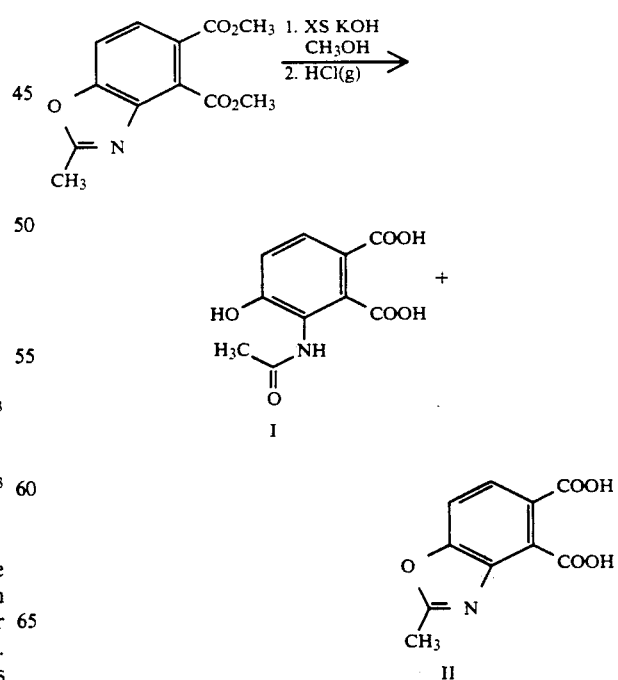

A mixture of dimethyl 2-methyl-5,6-benzoxazoledicarboxylate (8.33 g, 33.4 mmol), potassium hydroxide (4.88 g, 86.9 mmol) and methanol is stirred for 4.75 hours at 67° C., cooled and filtered. The white solid filter cake is set aside and the filtrate is concentrated in vacuo to give a pale yellow solid residue. Both solids are combined and dissolved in tetrahydrofuran, cooled to 0° C. and bubbled through with hydrogen chloride for 4 minutes, stirred for 4 hours at ambient temperatures and filtered. The white solid filter cake is air-dried to give the title product mixture, identified by NMR spectroscopy.

EXAMPLE 43

Preparation of 2-Methyl-4,5-benzoxazoledicarboxylic anhydride

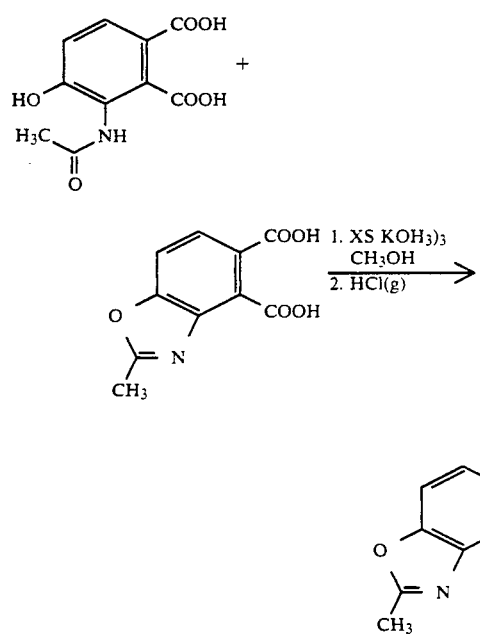

A 4:1 mixture of 3-acetamido-4-hydroxyphthalic acid and 2-methyl-4,5-benzoxazoledicarboxylic acid in acetic anhydride and concentrated sulfuric acid (0.10 mL) is stirred for 18 hours at 110° C., cooled and filtered. The white solid filter cake is air dried to give the title product, 5.39 g (77.1%), identified by NMR and IR spectral analyses.

EXAMPLE 44

Preparation of 3(and 2)-Acetamido-4(and 3)-hydroxy-2-(and 6)-(4-isopropyl-4-methyl-5-oxo-2-imidazolin-2-yl)benzoic acid and 4-(4-isopropyl-4-methyl-5-oxo-2-imidazolin-1-yl)-2-methyl-5-benzoxazolecarboxylic acid

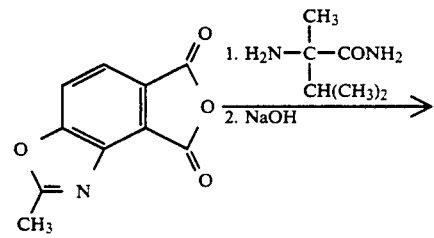

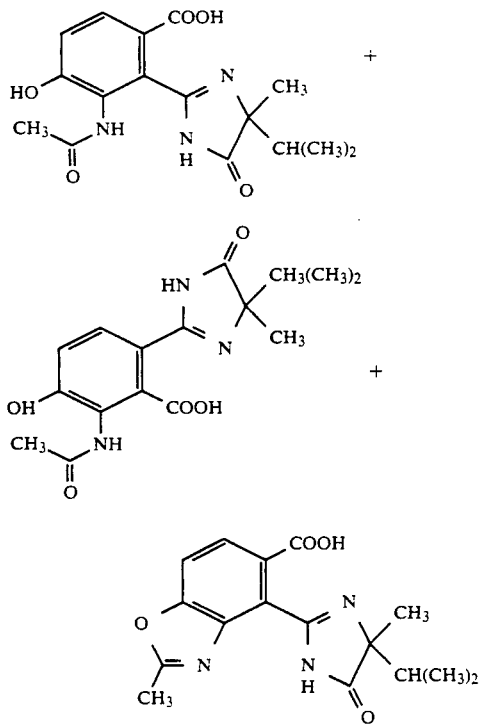

A mixture of 2-methyl-4,5-benzoxazoledicarboxylic anhydride (1.00 g, 4.92 mmol), α-methylvalinamide (0.640 g, 4.92 mmol) and dimethoxyethane is stirred for 4 hours at 35° C. and concentrated in vacuo to give an off-white solid residue. The residue is taken up in tetrahydrofuran and aqueous sodium hydroxide (4.06 mL, 5N, 20.3 mmol) and the resultant mixture is stirred for 90 minutes at 65° C., cooled and concentrated in vacuo. The aqueous residue is cooled, acidified to pH 1.5 with concentrated sulfuric acid, and extracted with ethyl acetate. The organic extracts are combined, dried (MgSO4) and concentrated in vacuo to afford the title product mixture as a white solid, 0.550 g, identified by NMR spectral analysis.

EXAMPLE 45

Preemergence Herbicidal Evaluation Of Test Compounds

The preemergence herbicidal activity of the present imidazolinyl benzoheterocyclic compounds of the present invention is demonstrated by the following tests in which the seeds of a variety of monocotyledenous and dicotyledenous plant species are individually mixed with potting soil and planted on top of approximately one inch of soil in one pint cups. After planting, the cups are sprayed with an aqueous acetone solution containing the test compound. Said test solution consist of a 50/50 acetone/water mixture and a test compound in sufficient quantity to provide the equivalent of about 0.016 kg/ha to 4.0 kg/ha of active compound when applied to the soil through a spray nozzle operating at 40 psi for a predetermined time. The treated cups are then placed on greenhouse benches and cared for in accordance with conventional greenhouse procedures.

From 4 to 5 weeks after treatment, the test cups are evaluated and rated according to the rating system set forth below. The herbicidal effectiveness of the compounds of the present invention is evident from the test results recorded in Table I below.

HERBICIDE RATING SCALE

Results of herbicide evaluations are expressed on a rating scale of 0-9. The scale is based upon a visual observation of plant stand, vigor, malformation, size, chlorosis and overall plant appearance as compared with a control.

| Rating | Meaning | % Control (Compared To Check) |
|---|---|---|
| 9 | Complete kill | 100 |
| 8 | Approaching Complete Kill | 91-99 |
| 7 | Good Herbicidal Effect | 80-90 |
| 6 | Herbicidal Effect | 65-79 |
| 5 | Definite Injury | 45-64 |
| 4 | Injury | 30-44 |
| 3 | Moderate Effect | 16-29 |
| 2 | Slight Effect | 6-15 |
| 1 | Trace Effect | 1-5 |
| 0 | No Effect | 0 |

When more than one test is evaluated, the results are reported as averaged values.

PLANT SPECIES USED

| Column Heading | Common Name | Scientific Name |
|---|---|---|
| BARNYARDGR | BARNYARDGRASS | *ECHINOCHLOA CURS-GALLI*, (L)BEAU |
| P NUTSEDGE | NUTSEDGE, PURPLE | *CYPERUS RONTUNDUS*, L. |
| WILD OATS | OAT, WILD | *AVENA FATUA*, L. |
| QUACKGRASS | QUACKGRASS | *AGROPYRON REPENS*, (L)BEAUV. |
| FLD BINDWD | BINDWEED, FIELD (RHIZOME) | *CONVOLVULUS ARVENSIS*, L. |
| MRNGLRY SP | MORNINGGLORY SPP. | *IPOMOEA* SPP. |
| VELVETLEAF | VELVETLEAF | *ABUTILON THEOPHRASTI*, MEDIC. |
| BARLEY | BARLEY, UNSPECIFIED | *HORDEUM VULGARE*, L. |
| WHT FENMAN | WHEAT, FENMAN | *TRITICUM AESTIVUM*, FENMAN |
| CORN FIELD | CORN, FIELD | *ZEA MAYS*, L. |

TABLE I

Preemergence Herbicidal Evaluation

| Compound Name | Rate kg/ha | Barn-yardgr | P Nut-sedge | Wild Oats | Quack-grass | Fld Bindwd | Mrnglry Sp | Velvet-leaf | Barley | Wht Fenman | Corn Field |
|---|---|---|---|---|---|---|---|---|---|---|---|
| Methyl 7-(4-isopropyl-4-methyl-5-oxo-2-imidazolin-2-yl)-6-benzofurancarboxylate | .250 | 5.0 | 2.0 | 3.0 | 2.0 | 8.0 | 7.0 | 6.0 | 1.0 | 2.0 | 1.0 |
|  | .125 | 2.0 | 0.0 | 0.0 | 1.0 | 5.0 | 5.0 | 0.0 | 0.0 | 0.0 | 0.0 |
| 7-(4-Isopropyl-4-methyl-5-oxo-2-imidazolin-2-yl)-6-benzothiophenecarboxylic acid | .500 | 0.0 | 7.0 | 0.0 | 1.0 | 9.0 | 8.0 | 7.0 | 1.0 | 5.0 | 3.0 |
|  | .250 | 0.0 | 8.0 | 0.0 | 1.0 | 9.0 | 8.0 | 6.0 | 1.0 | 1.0 | 3.0 |
|  | .125 | 0.0 | 1.0 | 0.0 | 1.0 | 5.0 | 5.0 | 3.0 | 0.0 | 0.0 | 2.0 |
|  | .063 | 0.0 | 0.0 | 0.0 | 1.0 | 7.0 | 3.0 | 2.0 | 0.0 | 0.0 | 2.0 |
| 2-(4-Isopropyl-4-methyl-5-oxo-2-imidazolin-2-yl)-3,4-(methylenedioxy)-benzoic acid | .500 | 8.5 | 9.0 | 8.3 | 9.0 | 9.0 | 8.0 | 8.0 | — | 9.0 | 8.8 |
|  | .125 | 6.5 | 9.0 | 7.0 | 9.0 | 8.3 | 7.8 | 7.0 | — | 7.0 | 8.5 |
|  | .063 | 4.0 | 7.3 | 6.3 | 7.5 | 7.0 | 6.8 | 5.8 | — | 6.0 | 7.3 |
|  | .032 | 1.0 | 4.0 | 3.5 | 6.0 | 3.5 | 4.0 | 3.5 | — | — | 3.0 |
| 9-Isopropyl-9-methyl-6H-1,3-dioxolo[4,5-g]-imidazo[2,1-a]isoin-dole-6,8(9H)dione | .500 | 9.0 | 9.0 | 8.0 | 9.0 | 9.0 | 8.0 | 8.0 | — | — | 9.0 |
|  | .250 | 7.0 | 9.0 | 6.0 | 9.0 | 9.0 | 8.0 | 8.0 | — | — | 8.0 |
|  | .125 | 3.0 | 8.0 | 3.0 | 5.0 | 7.0 | 7.0 | 7.0 | — | — | 7.0 |
|  | .063 | 2.0 | 8.0 | 0.0 | 5.0 | 7.0 | 6.0 | 3.0 | — | — | 3.0 |
| 8-Isopropyl-8-methyl-6H-1,3-dioxolo-[4,5-g]-imidazo[2,1-a]-isoin-dole-6,9(8H)-dione | 1.000 | 8.0 | 9.0 | 9.0 | 9.0 | 9.0 | 8.0 | 8.0 | — | 9.0 | 9.0 |
|  | .250 | 7.0 | 9.0 | 7.0 | 9.0 | 9.0 | 8.0 | 7.0 | — | 7.0 | 7.0 |
|  | .125 | 6.0 | 6.0 | 7.0 | 5.0 | 7.0 | 7.0 | 6.0 | — | 4.0 | 4.0 |
|  | .063 | 2.0 | 2.0 | 4.0 | 5.0 | 6.0 | 5.0 | 4.0 | — | 4.0 | 1.0 |
| Methyl 2-(4-isopropyl-4-methyl-5-oxo-2-imidazolin-2-yl)-3,4-(methylenedioxy)-benzoate | 2.000 | 9.0 | 7.5 | 9.0 | 7.0 | 9.0 | 8.0 | 7.5 | 8.0 | 7.0 | 7.5 |
|  | .500 | 8.0 | 6.0 | 8.5 | 4.0 | 8.0 | 7.0 | 6.5 | 5.5 | 5.0 | 6.5 |
|  | .250 | 6.5 | 4.5 | 8.5 | 2.5 | 7.0 | 6.0 | 4.0 | 4.0 | 4.0 | 4.0 |
|  | .125 | 3.0 | 1.5 | 8.5 | 0.0 | 2.5 | 3.0 | 2.0 | 1.5 | 3.0 | 3.0 |
| Furfuryl 2-(4-isopropyl-4-methyl-5-oxo-2-imidazolin-2-yl)piperonylate | 2.000 | 9.0 | 9.0 | 9.0 | 9.0 | 9.0 | 8.0 | 8.0 | 9.0 | 9.0 | 9.0 |
|  | .500 | 8.0 | 9.0 | 9.0 | 9.0 | 9.0 | 8.0 | 8.0 | 7.0 | 8.0 | 9.0 |
|  | .125 | 5.0 | 7.0 | 6.0 | 9.0 | 7.0 | 6.0 | 7.0 | 5.0 | 6.0 | 3.0 |
|  | .063 | 2.0 | 3.0 | 3.0 | 6.0 | 6.0 | 4.0 | 5.0 | 4.0 | 3.0 | 3.0 |
| 2-Propynyl 2-(4-isopropyl-4-methyl-5-oxo-2-imidazolin-2-yl)piperonylate | 2.000 | 9.0 | 9.0 | 9.0 | 9.0 | 9.0 | 8.0 | 8.0 | 9.0 | 9.0 | 8.0 |
|  | .500 | 8.0 | 9.0 | 8.0 | 9.0 | 9.0 | 8.0 | 8.0 | 8.0 | 8.0 | 7.0 |
|  | .125 | 5.0 | 5.0 | 8.0 | 6.0 | 8.0 | 7.0 | 6.0 | 5.0 | 6.0 | 5.0 |
|  | .063 | 2.0 | 5.0 | 5.0 | 6.0 | 7.0 | 7.0 | 6.0 | 4.0 | 4.0 | 4.0 |

EXAMPLE 46

Postemergence Herbicidal Evaluation Of Test Compounds

The postemergence herbicidal activity of the imidazolinyl benzoheterocyclic compounds of the present invention is demonstrated by the following tests wherein a variety of monocotyledenous and dicotyledenous plants are treated with solutions of the test compound in aqueous acetone. Said test solutions consist of a 50/50 acetone/water mixture containing 0.5% TWEEN® 20, a polyoxyethylene sorbitan monolaurate surfactant manufactured by Atlas Chemical Industries and a test compound in sufficient quantity to provide the equivalent of about 0.032 kg/ha to 8.00 kg/ha of active compound when applied to the plants through a spray nozzle operating at 40 psi for a predetermined time. In the tests, seedling plants are grown in jiffy flats for about 2 weeks. The plants are sprayed with the test solution, placed on greenhouse benches and cared for in the usual manner commensurate with conventional greenhouse practice.

From 4 to 5 weeks after treatment, the plants are examined and rated according to the rating system described hereinabove. The herbicidal effectiveness of the compounds of the present invention is evident from the data recorded in Table II below.

Where more than one test is performed for a given compound, the data are averaged.

| PLANT SPECIES USED | | |
|---|---|---|
| Column Heading | Common Name | Scientific Name |
| BARNYARDGR | BARNYARDGRASS | *ECHINOCHLOA CURSGALLI,* (L)BEAU |
| P NUTSEDGE | NUTSEDGE, PURPLE | *CYPERUS RONTUNDUS,* L. |
| WILD OATS | OAT, WILD | *AVENA FATUA,* L. |
| QUACKGRASS | QUACKGRASS | *AGROPYRON REPENS,* (L)BEAUV. |
| FLD BINDWD | BINDWEED, FIELD (RHIZOME) | *CONVOLVULUS ARVENSIS,* L. |
| MRNGLRY SP | MORNINGGLORY SPP. | *IPOMOEA* SPP. |
| VELVETLEAF | VELVETLEAF | *ABUTILON THEOPHRASTI,* MEDIC. |
| BARLEY | BARLEY, UNSPECIFIED | *HORDEUM VULGARE,* L. |
| WHT FENMAN | WHEAT, FENMAN | *TRITICUM AESTIVUM,* FENMAN |
| CORN FIELD | CORN, FIELD | *ZEA MAYS,* L. |

TABLE II

Preemergence Herbicidal Evaluation

| Compound Name | Rate kg/ha | Barn-yardgr | P Nut-sedge | Wild Oats | Quack grass | Fld Bindwd | Mrnglry Sp | Velvet-leaf | Barley | Wht Fenman | Corn Field |
|---|---|---|---|---|---|---|---|---|---|---|---|
| Methyl 7-(4-isopropyl-4-methyl-5-oxo-2-imidazolin-2-yl)-6-benzofurancarboxylate | .250 | 7.0 | — | 4.0 | 1.0 | 6.0 | 6.0 | 4.0 | 3.0 | 2.0 | 5.0 |
| 7-(4-Isopropyl-4-methyl-5-oxo-2-imidazolin-2-yl)-6-benzothiophenecarboxylic acid | 1.000 | 0.0 | 0.0 | 0.0 | 0.0 | 9.0 | 3.0 | 4.0 | 0.0 | 0.0 | 0.0 |
| | .500 | 0.0 | 0.0 | 0.0 | 0.0 | 5.0 | 7.0 | 3.0 | 0.0 | 0.0 | 0.0 |
| | .125 | 0.0 | 0.0 | 0.0 | 0.0 | 3.0 | 0.0 | 0.0 | 0.0 | 0.0 | 0.0 |
| | .032 | 0.0 | 0.0 | 0.0 | 0.0 | 0.0 | 0.0 | 0.0 | 0.0 | 0.0 | 0.0 |
| 2-(4-Isopropyl-4-methyl-5-oxo-2-imidazolin-2-yl)-3,4-(methylenedioxy)-benzoic acid | .500 | 9.0 | 7.3 | 9.0 | 8.0 | 9.0 | 7.8 | 7.5 | — | 8.0 | 8.5 |
| | .125 | 8.0 | 6.3 | 8.8 | 5.8 | 8.3 | 6.8 | 6.5 | — | 8.0 | 7.8 |
| | .063 | 7.0 | 4.5 | 8.0 | 2.0 | 6.0 | 5.5 | 5.8 | — | 7.0 | 7.3 |
| | .032 | 4.0 | 4.5 | 7.5 | 1.5 | 5.0 | 4.0 | 3.0 | — | 6.0 | 7.0 |
| 9-Isopropyl-9-methyl-6H-1,3-dioxolo[4,5-g]-imidazo[2,1-a]isoindole-6,8(9H)dione | .500 | 9.0 | 7.0 | 8.0 | 7.0 | 9.0 | 8.0 | 9.0 | — | — | 7.0 |
| | .250 | 9.0 | 7.0 | 9.0 | 0.0 | 9.0 | 8.0 | 8.0 | — | — | 6.0 |
| | .125 | 7.0 | 6.0 | 7.0 | 0.0 | 7.0 | 8.0 | 7.0 | — | — | 7.0 |
| | .063 | 6.0 | 5.0 | 5.0 | 0.0 | 7.0 | 8.0 | 7.0 | — | — | 7.0 |
| 8-Isopropyl-8-methyl-6H-1,3-dioxolo-[4,5-g]-imidazo[2,1-a]-isoindole-6,9(8H)-dione | 2.000 | 9.0 | 2.0 | 9.0 | 8.0 | 9.0 | 7.0 | 5.0 | — | 8.0 | 7.0 |
| | .500 | 8.0 | 2.0 | 9.0 | 6.0 | 9.0 | 5.0 | 4.0 | — | 7.0 | 1.0 |
| | .125 | 3.0 | 0.0 | 8.0 | 2.0 | 9.0 | 3.0 | 3.0 | — | 5.0 | 1.0 |
| | .063 | 1.0 | 0.0 | 2.0 | 1.0 | 3.0 | 1.0 | 2.0 | — | 3.0 | 2.0 |
| Methyl 2-(4-isopropyl-4-methyl-5-oxo-2-imidazolin-2-yl)-3,4-(methylenedioxy)-benzoate | 2.000 | 6.5 | 4.0 | 8.5 | 1.0 | 5.5 | 7.0 | 4.5 | 5.0 | 2.0 | 6.0 |
| | 1.000 | 6.5 | 3.0 | 8.0 | 0.5 | 3.0 | 6.0 | 3.5 | 3.5 | 2.0 | 3.0 |
| | .500 | 3.0 | 1.5 | 5.5 | 0.5 | 2.5 | 3.0 | 2.5 | 3.0 | 1.0 | 4.0 |
| | .250 | 1.0 | 0.0 | 4.0 | 0.5 | 3.0 | 1.5 | 0.5 | 2.5 | 1.0 | 2.5 |
| Furfuryl 2-(4-isopropyl-4-methyl-5-oxo-2-imidazolin-2-yl)piperonylate | 2.000 | 9.0 | 4.0 | 9.0 | 8.0 | 9.0 | 6.0 | 5.0 | 8.0 | 7.0 | 6.0 |
| | .500 | 5.0 | 3.0 | 8.0 | 4.0 | 9.0 | 6.0 | 3.0 | 6.0 | 7.0 | 3.0 |
| | .250 | 0.0 | 0.0 | 6.0 | 3.0 | 5.0 | 5.0 | 2.0 | 4.0 | 6.0 | 2.0 |
| | .125 | 0.0 | 0.0 | 3.0 | 2.0 | 4.0 | 2.0 | 1.0 | 1.0 | 4.0 | 1.0 |
| 2-Propynyl 2-(4-isopropyl-4-methyl-5-oxo-2-imidazolin-2-yl)piperonylate | 2.000 | 8.0 | 5.0 | 9.0 | 7.0 | 3.0 | 7.0 | 5.0 | 8.0 | 8.0 | 4.0 |
| | 1.000 | 7.0 | 5.0 | 9.0 | 8.0 | 9.0 | 6.0 | 3.0 | 4.0 | 7.0 | 4.0 |
| | .500 | 5.0 | 3.0 | 9.0 | 3.0 | 6.0 | 7.0 | 3.0 | 4.0 | 4.0 | 2.0 |
| | .125 | 0.0 | 0.0 | 4.0 | 2.0 | 2.0 | 3.0 | 2.0 | 2.0 | 4.0 | 0.0 |

What is claimed is:

1. A compound having the structure

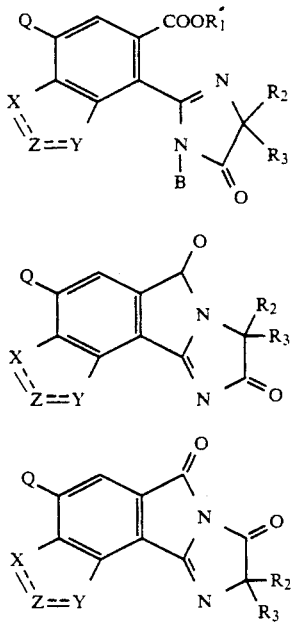

wherein
R₁ is hydrogen, di(C₁-C₄)alkylimino,
  C₁-C₁₂ alkyl optionally substituted with one to three of the following: C₁-C₄ alkoxy, C₁-C₄ alkylthio, halogen, hydroxy, C₃-C₆ cycloalkyl, benzyloxy, furyl, phenyl, optionally substituted with one nitro, one to three halogens, C₁-C₄ alkyl groups or C₁-C₄ alkoxy groups, carboxy, C₁-C₄ alkoxycarbonyl, cyano or tri(C₁-C₄)alkylammonium halide,
  C₃-C₁₂ alkenyl optionally substituted with one to three of the following: C₁-C₄ alkoxy, phenyl, halogen or C₁-C₄ alkoxycarbonyl,
  C₃-C₆ cycloalkyl optionally substituted with one to three C₁-C₄ alkyl groups,
  C₃-C₁₆ alkyl optionally substituted with one to three C₁-C₃ alkyl groups or
  a cation;
R₂ is C₁-C₄ alkyl;
R₃ is C₁-C₄ alkyl or C₃-C₆ cycloalkyl, and when R₂ and R₃ are taken together with the carbon to which they are attached they may represent C₃-C₆ cycloalkyl optionally substituted with methyl;
B is hydrogen, COR₄ or SO₂R₅ with the proviso that when B is COR₄ or SO₂R₅, R₃ is other than hydrogen or a cation;
R₄ is C₁-C₁₁ alkyl, chloromethyl or phenyl optionally substituted with halogen, nitro or C₁-C₄ alkyl;
R₅ is C₁-C₄ alkyl or phenyl optionally substituted with C₁-C₄ alkyl;
X, Y and Z are each independently CR₆, CR₇R₈, NR₉, N O or S with the provisos that at least one of X, Y and Z must be O or S, at least one of X, Y and Z must be CR₆ or CR₇R₈, when X or Y are O or S, then Z cannot be O or S and when X and Y are both O and Z is CR₇R₈, the structure must be a, c or e;
the ----- configuration represents either a single bond or a double bond with the proviso that when any of X, Y or Z is CR₇R₈, NR₉, O or s, then the configuration attached thereto represents a single bond and with the further proviso that at least one of the ----- configurations represents a single bond;
R₆, R₇ and R₈ are each independently hydrogen, halogen, C₁-C₄ alkoxy or C₁-C₄ alkyl optionally substituted with one hydroxy or one to three halogens, C₁-C₄ alkoxy groups, or C₁-C₄ alkylthio groups;
R₉ is hydrogen or C₁-C₄ alkyl optionally substituted with one hydroxy or one to three halogens, C₁-C₄ alkoxy groups or C₁-C₄ alkylthio groups;
Q is hydrogen, halogen, C₁-C₄ alkoxy or C₁-C₄ alkyl optionally substituted with one or more of the following: halogen, C₁-C₄ alkoxy, C₁-C₄ alkylthio, or C₂-C₄ alkenyl;
the optical isomers thereof when R₂ and R₃ are not the same or when R₇ and R₈ are not the same;
the tautomers and geometric isomers thereof and the acid addition salts thereof except when R₁ is a salt forming cation.

2. The compound according to claim 1 wherein Z is CR₆ or CR₇R₈.

3. The compound according to claim 2 wherein R₁ is hydrogen or a cation; R₂ is methyl; R₃ is isopropyl and R₆, R₇, R₈, B and Q are hydrogen.

4. The compound according to claim 2 wherein X is O, Y is N and Z is CR₆.

5. The compound according to claim 4, 4-(4-isopropyl-4-methyl-5-oxo-2-imidazolin-2-yl)-2-methyl-5-benzoxazolecarboxylic acid.

6. The compound according to claim 2 wherein X and Y are both O and Z is CR₇R₈.

7. The compound according to claim 6 wherein R₁ is hydrogen, C₁-C₄ alkyl optionally substituted with halogen, C₁-C₃ alkoxy, hydroxy, furyl, phenyl or halophenyl, C₂-C₆ alkenyl, C₃-C₆ cycloalkyl; C₂-C₆ alkynyl or a cation; R₂ is methyl; R₃ is isopropyl and R₆, R₇, B and Q are hydrogen.

8. The compound according to claim 7, 2-(4-isopropyl-4-methyl-5-oxo-2-imidazolin-2-yl)piperonylic acid.

9. The compound according to claim 6, 8-isopropyl-8-methyl-6H-1,3-dioxolo[4,5-g]imidazo[2,1a]isoindole-6,9(8H)-dione.

10. The compound according to claim 6, 9-isopropyl-9-methyl-6H-1,3-dioxolo[4,5-g]imidazo[2,1-a]isoindole-6,8(9H)-dione.

11. A method for the control of monocotyledenous and dicotyledenous plant species which comprises applying to the foliage of said plant species or to the soil or water containing seeds or other propagating organs of said plant species a herbicidally effective amount of a compound having the structure as described in claim 1.

12. The method according to claim 11 wherein Z is CR₆ or CR₇R₈.

13. The compound according to claim 12 wherein X and Y are both O and Z is CR₇R₈.

14. The method according to claim 11 wherein the compound is applied to the foliage of said plant species or to the soil or water containing seeds or other propagating organs of said plant species at a rate of about 0.032 kg/ha to 8.0 kg/ha.

15. A herbicidal composition which comprises an inert solid or liquid diluent and a herbicidally effective amount of a compound having the structure as described in claim 1.

16. The herbicidal composition according to claim 15 wherein X and Y are both O and Z is CR₇R₈.

* * * * *